(12) United States Patent
Zeiner et al.

(10) Patent No.: US 8,927,245 B2
(45) Date of Patent: Jan. 6, 2015

(54) LIGATION METHOD EMPLOYING EUKARYOTIC TRNA LIGASE

(75) Inventors: Gusti Zeiner, San Mateo, CA (US); Robert A. Ach, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 414 days.

(21) Appl. No.: 13/327,572

(22) Filed: Dec. 15, 2011

(65) Prior Publication Data
US 2012/0156730 A1 Jun. 21, 2012

Related U.S. Application Data

(60) Provisional application No. 61/424,008, filed on Dec. 16, 2010.

(51) Int. Cl.
*C12N 9/00* (2006.01)
*C07H 21/02* (2006.01)

(52) U.S. Cl.
USPC ........ 435/183; 435/91.3; 536/23.1; 536/24.2; 536/24.5; 536/24.1

(58) Field of Classification Search
None
See application file for complete search history.

(56) References Cited

U.S. PATENT DOCUMENTS

2010/0167954 A1 7/2010 Earnshaw et al.

OTHER PUBLICATIONS

Mortazavi et al (Nature Methods 5(7) 621-628, 2008).*
Shelton et al (Inorg. Chem. 3:4295-4299, 1991).*
Apostol, et al., "Deletion analysis of a multifunctional yeast tRNA ligase polypeptide. Identification of essential and dispensable functional domains", J Biol Chem, 1991, 266:7445-55.
Englert, et al., "Plant tRNA ligases are multifunctional enzymes that have diverged in sequence and substrate specificity from RNA ligases of other phylogenetic origins", Nucleic Acids Res, 2005, 33:388-99.
Nandakumar, et al., "RNA repair: an antidote to cytotoxic eukaryal RNA damage", Mol Cell, 2008, 31:278-86.
Phizicky, et al., "Saccharomyces cerevisiae tRNA ligase. Purification of the protein and isolation of the structural gene", J Biol Chem, 1986, 261:2978-86.
Sawaya, et al., "Genetic and biochemical analysis of the functional domains of yeast tRNA ligase", J Biol Chem, 2003, 278:43928-38.
Schutz, et al., "Capture and sequence analysis of RNAs with terminal 2',3'-cyclic phosphates", RNA, 2010, 16:621-31.
Sugahara, et al., "In silico screening of archaeal tRNA-encoding genes having multiple introns with bulge-helixbulge splicing motifs", RNA, 2007, 13:671-81.
Ho, T, et al., "A simplified method for cloning of short interfering RNAs from *Brassica juncea* infected with Turnip mosaic potyvirus and Turnip crinkle carmovirus", Journal of Virological Methods, 2006, 136:217-23.
Lu, C, et al., "Construction of small RNA cDNA libraries for deep sequencing", Methods, 2007, 43:110-17.
Saunders, R D., et al., "PCR amplification of DNA microdissected from a single polytene chromosome band : a comparison with conventional microcloning", Nucleic Acids Research, 1989, 17:9027-37.
PCTUS2011065268, International Search Report dated Sep. 19, 2012, 3 Pages.
Ambion, "RNA Fragmentation Reagents", Ambion Catalog,2008, pp. 1-2.

* cited by examiner

*Primary Examiner* — Richard Schnizer

(57) ABSTRACT

Provided herein is a method of preparing an RNA sample comprising: a) obtaining an RNA sample comprising: i. long RNA molecules that may be unfragmented or fragmented to contain 5'-OH group and a 2'-3'-cyclic phosphate group; and ii. short RNA molecules that comprise a 5' phosphate group and a 3' OH group; and b) contacting the RNA sample with an adaptor comprising either a 2'-PO group and 3'-OH group or a 2',3'-cyclic phosphate group in the presence of a eukaryotic tRNA ligase, thereby producing a ligated RNA sample in which a) the short RNA molecules are selectively ligated to the adaptor or b) the short RNA molecules and long RNA fragments are selectively ligated to the adaptor.

18 Claims, 11 Drawing Sheets

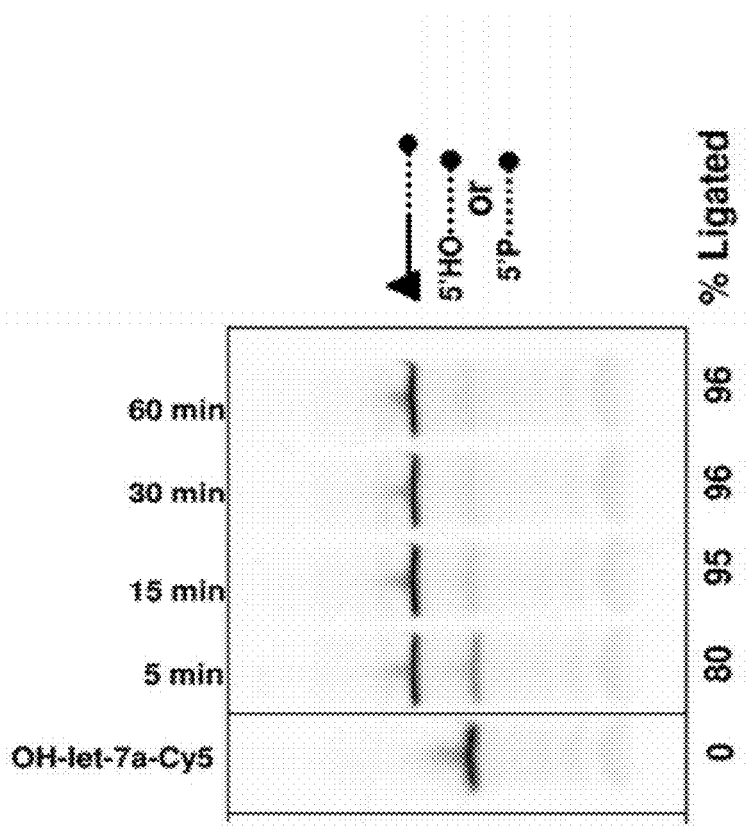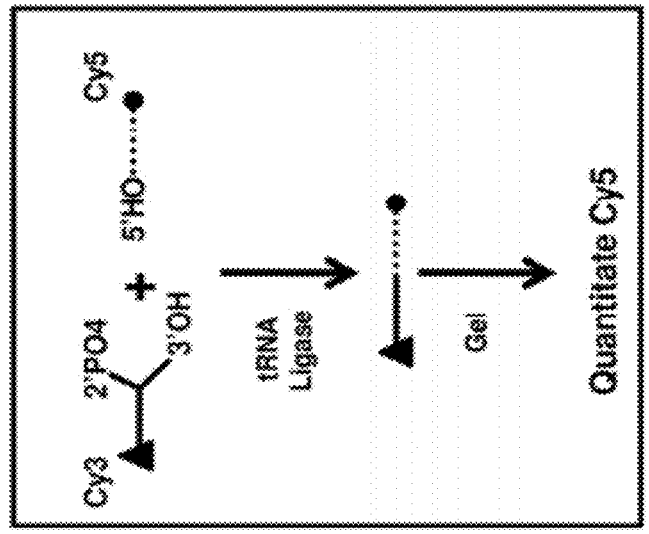
Fig. 5

LIGATION METHOD EMPLOYING EUKARYOTIC TRNA LIGASE

CROSS REFERENCE TO RELATED APPLICATIONS

Pursuant to 35 U.S.C. §119(e), this application claims priority to the filing date of U.S. Provisional Patent Application Ser. No. 61/424,008 filed Dec. 16, 2010, the disclosure of which application is herein incorporated by reference.

INTRODUCTION

Total RNA samples typically contain RNA molecules that vary in length. For example, a typical total RNA sample obtained from mammalian cells may contain mRNA molecules (which generally range in size from a few hundred bases to several kb), lincRNA molecules (which are classified as being at least 200 bases in length), 18S and 28S rRNA molecules (which are approximately 1.9 kb and 5 kb, respectively), tRNA molecules (which are generally below 100 nt in length), and a variety of small RNA molecules (e.g., short interfering RNAs, microRNAs, tiny non-coding RNAs, small modulators RNAs and piwi-interacting RNAs) some of which are in the range of 18 to 25 bases in length.

SUMMARY

Provided herein is a method of preparing an RNA sample comprising: a) obtaining an RNA sample comprising: i. long RNA molecules that may be unfragmented or fragmented, where the fragmented long RNAs contain a 5'-OH group and a 2'-3'-cyclic phosphate group; and ii. short RNA molecules that comprise a 5' phosphate group and a 3' OH group; and b) contacting the RNA sample with an adaptor comprising either a 2'-PO group and 3'-OH group or a 2',3'-cyclic phosphate group in the presence of a eukaryotic tRNA ligase. Depending on whether the sample is fragmented or not, the ligation step produces a ligated RNA sample in which a) the short RNA molecules are selectively ligated to the adaptor or b) the short RNA molecules and long RNA fragments are selectively ligated to the adaptor.

In some embodiments the method comprises: a) obtaining a fragmented RNA sample comprising: i. RNA fragments of long RNA molecules, wherein the fragments comprise a 5'-OH group and a 2'-3'-cyclic phosphate group; and ii. unfragmented short RNA molecules that comprise a 5' phosphate group and a 3' OH group; and b) contacting the fragmented RNA sample with an adaptor or adaptors comprising a 5'-PO and/or a 3' terminus comprising either a 2'-PO group and 3'-OH group or a 2',3'-cyclic phosphate group in the presence of a eukaryotic tRNA ligase, thereby producing a ligated RNA sample. A kit for performing the method is also provided.

Also provided is a of preparing an RNA sample comprising: a) obtaining an unfragmented RNA sample comprising: i. long RNA molecules; and ii. short RNA molecules that comprise a 5' phosphate group and a 3' OH group; and b) contacting the fragmented RNA sample with an adaptor comprising a blocked 5' end and either a 2'-PO group and 3'-OH group or a 2',3'-cyclic phosphate group in the presence of a eukaryotic tRNA ligase, thereby producing a ligated RNA sample in which the short RNA molecules are selectively ligated to the adaptor.

This disclosure also provides a method for preventing the formation of 5'-adaptor:3'-adaptor "adaptor-dimer" ligation products that do not contain an RNA insert, either of fragmented longer RNA or miRNA origin.

In one embodiment, the method may comprise: a) obtaining a first single stranded adaptor and a second single stranded adaptor, wherein the first adaptor and the second adaptors each contain partial recognition sites for a homing endonuclease and, when ligated together in the absence of an intervening insert RNA, create an adaptor dimer containing a recognition site for the homing endonuclease; b) ligating the first single stranded adaptor to a first end the of the RNA molecules of an RNA sample; c) ligating the second adaptor to the end the of the RNA molecules in the sample; d) producing double stranded cDNA from the product of step c); and e) cleaving the double stranded cDNA using the homing endonuclease, thereby removing adaptor dimers from the sample. This method may further include subjecting the cleaved sample to PCR using primers that hybridize to the adaptor sequences.

In an alternative embodiment, the method may comprise: a) ligating the first single stranded adaptor to a first end the of the RNA molecules of an RNA sample; b) hybridizing the first single stranded adaptor to a complementary oligonucleotide to make a duplex that does not contain an ligatable overhang of the single stranded adaptor, thereby removing the first single stranded adaptor as a substrate for a future ligation; and c) ligating a second adaptor to the other end the of the RNA molecules in the RNA sample using a eukaryotic tRNA ligase, thereby producing an RNA sample that has adaptors ligated to both ends. These adaptors could optionally contain partial homing endonuclease recognition elements as to enable both of the above methods of adaptor-dimer removal.

BRIEF DESCRIPTION OF THE FIGURES

FIG. 1A shows the domain structure of wild type eukaryotic tRNA ligase; CPD=2',3'-cyclic phosphodiesterase. FIG. 1B outlines of the three enzymatic activities of wild type eukaryotic tRNA ligase.

FIG. 2A shows the domain structure of an exemplary modified eukaryotic tRNA ligase lacking a functional cyclic phosphodiesterase domain (point-mutation denoted by an asterix). FIG. 2B schematically illustrates a two step method that can be used to generate a total RNA library suitable for microarray profiling with an RNLΔCPD enzyme. First, total RNA is fragmented with $Mg^{2+}$ and heat. Second, RNLΔCPD enzyme is added along with a universal 5' fluorophore-conjugated adapter probe. The kinase domain of the RNLΔCPD enzyme converts the 5' OH of the fragmented large RNA to 5' $PO_4$. Both miRNA and the repaired fragmented large RNA participate in a ligation reaction with the fluorescent 5' adapter probe. As the 3' terminus of the fragmented RNA is still in the 2',3'-cyclic phosphate group form, this 3' terminus cannot participate in ligation. Similarly, as the miRNA has a 3'OH group but no 2'PO group, this 3' terminus cannot participate in ligation.

FIG. 4A shows the domain structure of an exemplary modified eukaryotic tRNA ligase lacking a functional kinase (point-mutation denoted by an asterix). FIG. 4B schematically illustrates a three step method for generating a mRNA/ncRNA cDNA library suitable for cRNA production and microarray profiling. First, total RNA is fragmented with $Mg^{2+}$ and heat. Second, RNLΔkinase is added along with a 3' adapter probe. The cyclic phosphodiesterase domain of RNLΔkinase resolves the 2',3-cyclic phosphate of the fragmented large RNA to 2'PO and 3'OH. 2'PO-containing fragmented RNAs are now a substrate for ligation to the 3' adapter by RNLAkinase. cDNA can be primed off the 3' adapter to incorporate a T7 promoter suitable for cRNA production followed by microarray hybridization. As the miRNA has a 3'OH group but no 2'PO group, this 3' terminus cannot participate in ligation.

FIG. 5 shows the results of a time course that indicates the efficiency of the enzyme.

DEFINITIONS

Figure 1:
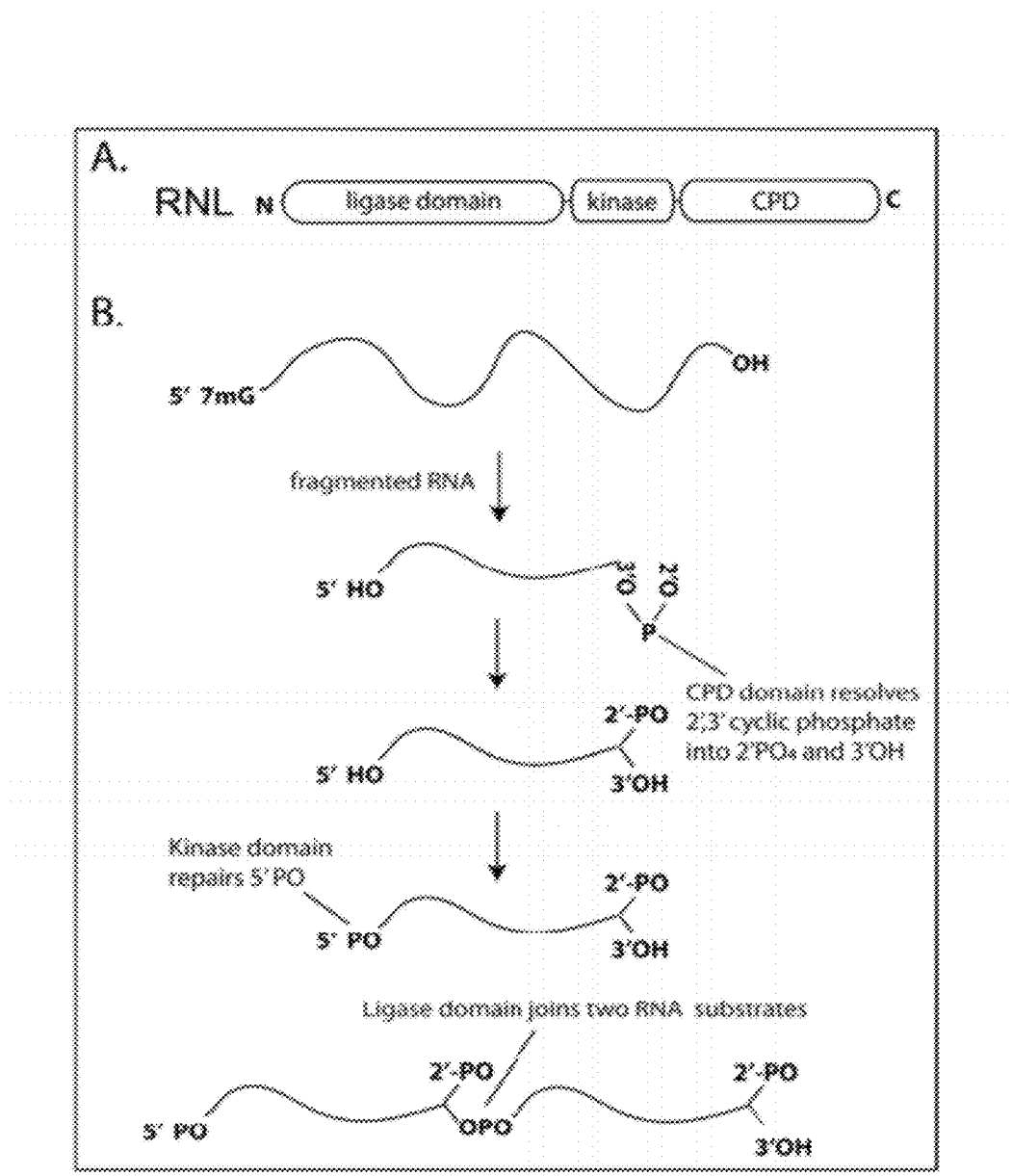
FIGS. 1A and 1B.

The term "RNA sample", as used herein, relates to a mixture of materials, typically, although not necessarily, in liquid form, containing one or more RNA molecules. An RNA sample may be obtained from cells, e.g., mammalian cells, for example. An RNA sample may contain a population of different RNA molecules, in which case it may contain more than 1,000, more than 10,000, more than 50,000, or more than 100,000 up to 1M or more different species of RNA, i.e., RNA molecules of different sequence. An RNA sample may contain long RNA molecules, which are RNA molecules that are at least 50 nt in length. Long RNA molecules include mRNA molecules, rRNA molecules, tRNA molecules, pre-miRNAs, snRNAs and long non-coding RNA molecules such as large intergenic RNA (lincRNA) molecules. Some long RNA molecules may be in the range of 50 to 10 kb in length, e.g., 200 nt to 10 kb in length. An RNA sample may also contain short RNA molecules which are RNA molecules that are below 50 nt in length. Short RNA molecules a variety of small non-coding regulatory RNAs that may be generically referred herein to as "small RNAs", i.e, short interfering RNAs, microRNAs, tiny non-coding RNAs piwi-interacting small RNAs (piRNAs) and small modulatory RNAs.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine and thymine (G, C, A and T, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers. Oligonucleotides may be 5 to 20, 11 to 30, 31 to 40, 41 to 50, 51-60, 61 to 70, 71 to 80, 80 to 100, 100 to 150 or 150 to 200, up to 500 nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be surface-tethered, i.e., immobilized on a surface of a substrate, where the substrate can have a variety of configurations, e.g., a sheet, bead, or other structure. In certain embodiments, a probe may be present on a surface of a planar support, e.g., in the form of an array.

The phrase "surface-bound nucleic acid" refers to a nucleic acid that is immobilized on a surface of a solid substrate, where the substrate can have a variety of configurations, e.g., a sheet, bead, or other structure. In certain embodiments, the nucleic acid probes employed herein are present on a surface of the same planar support, e.g., in the form of an array.

The phrase "labeled population of nucleic acids" refers to mixture of nucleic acids that are detectably labeled, e.g., fluorescently labeled, such that the presence of the nucleic acids can be detected by assessing the presence of the label.

The term "array" encompasses the term "microarray" and refers to an ordered array presented for binding to nucleic acids and the like.

An "array," includes any two-dimensional or three-dimensional arrangement of addressable regions, e.g., spatially addressable regions or optically addressable regions, bearing nucleic acids, particularly oligonucleotides or synthetic mimetics thereof, and the like. In some cases, the addressable regions of the array may not be physically connected to one another, for example, a plurality of beads that are distinguishable by optical or other means may constitute an array. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 $cm^2$ or even less than 10 $cm^2$, e.g., less than about 5 $cm^2$, including less than about 1 $cm^2$, less than about 1 $mm^2$, e.g., 100 $\mu m^2$, or even smaller. For example, features may have widths (that is, diameter, for a round spot) in the range from a 5 $\mu m$ to 1.0 cm. In other embodiments each feature may have a width in the range of 1.0 $\mu m$ to 1.0 mm, usually 5.0 $\mu m$ to 500 and more usually 10 $\mu m$ to 200 $\mu m$. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 $cm^2$, or even less than 50 $cm^2$, 5 $cm^2$, 1 $cm^2$, 0.5 $cm^2$, or 0.1 $cm^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. Patent Application Publication No. 20040203138 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$," refers to the melting temperature an oligonucleotide duplex at which half of the duplexes remain hybridized and half of the duplexes dissociate into single strands. The $T_m$ of an oligonucleotide duplex may be experimentally determined or predicted using the following formula $T_m=81.5\pm16.6(\log_{10}[Na^+])+0.41$ (fraction G+C)−(60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other more advanced models that depend on various parameters may also be used to predict $T_m$ of oligonucleotide duplexes may also be used depending on various hybridization conditions.

As used herein, the term "$T_m$-matched" refers to a plurality of nucleic acid duplexes having $T_m$s that are within a defined range, e.g. ±5° C., ±10° C., or ±15° C.

The term "hybridization conditions" as used herein refers to hybridization conditions that are sufficient to anneal an oligonucleotide of a sufficient length to a probe that is complementary to a nucleotide sequence of the probe. The hybridization conditions provide for dissociation of duplexes that anneal over a short length of region (e.g. less than 50, less than 40, less than 30, or less than 20 contiguous nucleotides). Such conditions may differ from one experiment to the next depending on the length and the nucleotide content of the complementary region. In certain cases, the temperature for low-stringency hybridization may be 5°-10° C. lower than the calculated Tm of the resulting duplex under the conditions used.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

As used herein, the term "data" refers to refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

If a nucleic acid probe "corresponds to" or is "for" a certain RNA, the nucleic acid probe base pairs with, i.e., specifically hybridizes to, that RNA. As will be discussed in greater detail below, a nucleic acid probe for a particular RNA and the particular RNA, or complement thereof, contains at least one region of contiguous nucleotides that is identical in sequence.

As used herein, the term "total cellular RNA" is an RNA sample that contains at least tRNA, rRNA, mRNA, lincRNA and small RNA.

As used herein, the term "depleted", in the context of a total cellular RNA sample that has been depleted for tRNA, rRNA, or another type of RNA, is total cellular RNA sample from which tRNA, rRNA, or another type of RNA has been subtracted, i.e., removed.

As used herein, the term "initial RNA sample" is an RNA sample that has not been exposed to fragmentation conditions and that contains intact RNA molecules. Such a sample may contain, for example, total cellular RNA or a total cellular RNA that has been depleted for rRNA and/or tRNA, or another type of RNA. An initial RNA sample contains at least one type of intact long RNA and one type of short RNA.

As used herein, the term "fragmented RNA sample" is a sample that contains fragments of RNA. A fragmented RNA sample can made from an initial RNA sample by exposing the initial RNA sample to fragmentation conditions. Fragmented RNA samples include RNA that has been extracted from a formalin-fixed paraffin embedded tissue (FPET) sample.

As used herein, the term "long RNA molecules" refers to RNA molecules that are at least 50 nt in length. Long RNA molecules include mRNA molecules, rRNA molecules, tRNA molecules, pre-miRNAs, snRNAs and long non-coding RNA molecules such as large intergenic RNA (lincRNA) molecules. Some long RNA molecules may be in the range of 50 to 10 kb in length, e.g., 200 nt to 10 kb in length.

As used herein, the term "short RNA molecules" refers to RNA molecules that are below 50 nt in length. Short RNA molecules include tRNA molecules and a variety of small non-coding regulatory RNAs generically referred herein to as "small RNAs", i.e, short interfering RNAs, microRNAs, tiny non-coding RNAs piwi-interacting small RNAs (piRNAs) and small modulatory RNAs.

As used herein, the term "fragments of long RNA molecules" refer to RNA fragments that are obtained by fragmentation of long RNA molecules. Depending on how fragmentation is done, fragments of long RNA molecules may have a 5'OH group and a 2',3' cyclic phosphate group at the 3' terminus.

As used herein, the term "fragmentation conditions" refer to an environment or an agent that induces non-sequence specific fragmentation of long RNA molecules. As will be described in greater detail below, when fragmenting a sample containing both long RNA molecules and short RNA molecules, the fragmentation conditions can be tailored to provide for fragmentation of long RNA molecules without significant fragmentation of short RNA molecules.

As used herein, the term "adaptor" refers to an oligonucleotide that may be composed of any type of nucleotide. An adaptor may be, e.g., an RNA adaptor, a DNA adaptor, or it may be composed of both ribonucleotides and deoxyribonucleotides or analogs thereof. An adaptor may be labeled or unlabeled and in certain cases may be of 5-50 bases, e.g., 6 to 12 bases, in length or longer depending on the application.

As used herein, the terms "5'-OH" and "5'-hydroxyl" refers to a nucleotide at the 5' terminus of a nucleic acid, where the nucleotide has a hydroxyl group at the 5' position.

As used herein, the terms "3'-OH" and "3'-hydroxyl" refers to a nucleotide at the 3' terminus of a nucleic acid, where the nucleotide has a hydroxyl group at the 3' position.

As used herein, the term "3'-P" or "3'-phosphate" refers to a nucleotide at the 3' terminus of a nucleic acid, where the nucleotide has a phosphate group at the 3' position.

As used herein, the term "5'-P" or "5'-phosphate" refers to a nucleotide at the 5' terminus of a nucleic acid, where the nucleotide has a phosphate group at the 5' position.

As used herein, the terms "2'-PO and 3'-OH" and "2'-phosphate and 3'-hydroxyl", in the context of a 3' terminus, refers to a nucleotide at the 3' terminus of a nucleic acid, where the sugar moiety of the nucleotide has both a phosphate group at the 2' position and a hydroxyl group at the 3' position.

As used herein, the term "2',3'-cyclic phosphate", in the context of a 3' terminus comprising 2',3'-cyclic phosphate, refers to a nucleotide at the 3' terminus of a nucleic acid, where the sugar moiety of the nucleotide has a phosphate group connected to the 2' and 3' positions, as shown below:

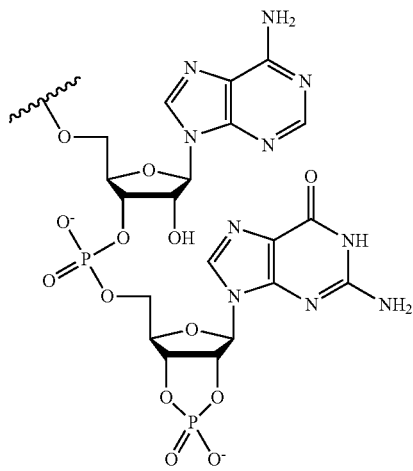

As used herein, the term "eukaryotic tRNA ligase" refers to a multifunctional enzyme that has: a) a ligase activity that catalyzes ligation of the 5' terminus of a nucleic acid having a 5'-phosphate to the 3' terminus of a nucleic acid having a 3' terminus having a 2'-phosphate and a 3'-hydroxyl to produce a ligation product that contains a 2' phosphate at the site of ligation; and, optionally b) a cyclic phosphodiesterase (CPD) activity that catalyzes the hydrolysis of a 2',3'-cyclic phosphate group to produce a 2'-phosphate and 3'-hydroxyl; and/or c) a kinase activity that catalyzes the phosphorylation of a 5'-hydroxyl to produce a 5'-phosphate. Wild type tRNA ligase enzymes have all three activities and are arranged as follows: a N-terminal ligase module, a central kinase module and a C-terminal 2'3'-cyclic phospodiesterase module. Such enzymes have been identified and characterized in yeast and plants, and are expected to be present in a number of other eukaryotes, e.g., mammals and archebacteria (see, e.g., Ramirez RNA 2008 14: 1737-45; Englert Nuc. Acids Res. 2005 33: 388-399; Sawaya J. Biol. Chem. 2003 278: 43928-43928; Apostol J. Biol. Chem 1991 266: 7445-7455; Phizicky J. Biol. Chem. 1986 261: 2978-2986; Nandakumar Mol. Cell. 2008 31: 278-286; Sugahara RNA 2007 13: 671-681; and Schutz RNA 2010 16: 621-631). As will be described in greater detail below, a eukaryotic tRNA ligase employed in a subject method may only have the ligase activity and, optionally, the kinase and/or cyclic phosphodiesterase activity. Thus, in particular cases, the eukaryotic tRNA ligase used in the method may minimally have a ligase domain having an amino acid sequence that is at least 80% to the amino acid of the ligase domain of a wild type eukaryotic tRNA ligase. The ligase domain is sufficient to catalyze ligation of the 5' terminus of a nucleic acid having a 5'-phosphate to the 3' terminus of a nucleic acid having a 3' terminus having a 2'-phosphate and a 3'-hydroxyl to produce a ligation product that contains a 2' phosphate at the site of ligation. The 2'-phosphate group may be removed by a 2'-phosphate group-specific specific phosphotransferase in the presence of NAD$^+$, or with a non-specific alkaline phosphatase, if necessary (Culver J. Biol. Chem. 1997: 13203-13210; Schutz RNA 2010 16: 621-631).

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Sample Analysis

Certain embodiments of the method involve fragmenting an initial sample of RNA that contains intact long RNA and intact short RNA to obtain a fragmented RNA sample. The long RNA in the initial sample at least 50 nucleotides in length and may include cellular mRNA, long non-coding RNAs (such as lincRNA) and/or tRNA and rRNA, for example. The defining characteristics of mRNA, rRNA and rRNA are well known. lincRNA is relatively newly discovered, and is believed to be involved in regulating wide variety of processes, e.g, embryonic stem cell pluripotency, cell proliferation, cancer and chromatin structure. This class of molecules is reviewed by Tingeras (Nature Biotechnology 2009 27: 346-347). The short RNA in the initial sample of less than 50 nucleotides in length and include and a variety of small non-coding regulatory RNAs generically referred herein to as "small RNAs", i.e, short interfering RNAs, microRNAs, tiny non-coding RNAs, piwi-interacting small RNAs (piRNAs) and small modulatory RNAs. Small RNAs are a group of non-coding regulatory RNAs that have defined sequences and that are in the range of 18-31 nucleotides (nts) in length. Many small RNAs are approximately 19-25 nts in length.

Small RNAs are generally reviewed in Novina et al (Nature 2004 430:161-164) and may be classified in at least five groups: a) short interfering RNAs (siRNAs), b) micro-RNAs (miRNAs), c) tiny non-coding RNAs (tncRNAs), d) piwi-interacting RNAs (piRNAs) and e) small modulator RNAs (smRNAs). siRNAs are a class of double stranded RNAs of approximately 21-22 nt in length, generated from double stranded RNAs. siRNAs are thought to silence gene expression by promoting the cleavage of mRNAs. miRNAs, on the other hand, are a class of single stranded RNAs of approximately 19-25 nt in length. miRNAs appear to be evolutionary conserved and are thought to silence gene expression by inhibiting translation. tncRNAs are a class of RNAs that are about 20-22 nucleotides. tncRNAs appear to be developmentally regulated, although their function is unknown. smRNAs are double stranded RNAs involved in regulating neuron-specific gene expression in adult neurons. piRNA forms RNA-protein complexes through interactions with Piwi proteins.

miRNAs are of particular interest. The sequences of several hundred miRNAs from a variety of different species, including humans, may be found at the microRNA registry (Griffiths-Jones, Nucl. Acids Res. 2004 32:D109-D111), and at the miRBase hosted by the Faculty of Life science at the University of Manchester (UK). The sequences of all of the microRNAs deposited at the microRNA registry, including 227 microRNA sequences from humans (see Lagos-Quintana et al, Science 294:853-858(2001); Grad et al, Mol Cell 11:1253-1263(2003); Mourelatos et al, Genes Dev 16:720-728(2002); Lagos-Quintana et al, Curr Biol 12:735-739 (2002); Lagos-Quintana et al, RNA 9:175-179(2003); Dostie et al, RNA 9:180-186(2003); Lim et al, Science 299:1540 (2003); Houbaviy et al, Dev Cell 5:351-358(2003); Michael et al, Mol Cancer Res 1:882-891(2003); Kim et al, Proc Natl Acad Sci USA 101:360-365(2004); Suh et al, Dev Biol 270: 488-498(2004); Kasashima et al, Biochem Biophys Res Commun 322:403-410(2004); and Xie et al, Nature 434:338-345(2005)), are incorporated herein by reference. The methods and compositions described above and below may be used to detect any of the microRNAs deposited at the microRNA registry, as well as others. As will be described in greater detail below, the nucleic acid probes described herein are particularly useful for the detection of small RNAs of 18-31 nucleotides.

As noted above, the method comprises obtaining a fragmented RNA sample comprising: i. RNA fragments of long RNA molecules, wherein the fragments comprise a 5'-OH group and a 2'-3'-cyclic phosphate group; and ii. unfragmented short RNA molecules that comprise a 5' phosphate group and a 3' OH group. The short RNA molecules naturally exist in the cell as molecules that contain a 5' phosphate group and a 3' OH group. As such, no further modification of those molecules is necessary. However, in particular cases, the short RNA molecules may or may not be treated with an enzyme, e.g., a kinase, to further ensure that the ends of those molecules contain 5' phosphate group and a 3' OH group. The long RNA molecules, on other hand, are fragmented to produce fragments containing a 5'-OH group and a 3' terminus having a 2'-3'-cyclic phosphate group.

In general terms, a fragmented RNA sample is made by exposing an initial RNA sample comprising intact long RNA molecules and short RNA molecules to fragmentation conditions that favor (e.g., maximize) fragmentation of the long RNA molecules relative to fragmentation of the short RNAs molecules. The fragments produced by this method contain 5'-OH and a 3' terminus having a 2'-3'-cyclic phosphate group. While there are other ways of producing such fragments, one embodiment involves exposing an initial RNA sample (which may contain, for example, total cellular RNA, total RNA that has been depleted for one or more types of RNA (e.g., rRNA and/or tRNA), or mRNA and small RNA, long non-coding RNA and small RNA, for example, although other combinations are contemplated) to a metal ion at a temperature of at least 50° C. for a suitable period of time.

Methods for fragmenting RNA to produce fragments that contain 5'-OH group and a 3' terminus having a 2'-3'-cyclic phosphate group include chemical, enzymatic or thermal fragmentation methods, protocols for which are known (see, e.g., Chandler et al, Appl. Environ. Microbiol. 2003 69:2950-2958, Guschin et al Appl. Environ. Microbiol. 1997 63:2397-2402; Kelly et al, Anal. Biochem. 2002 311:103-118, Liu et al Environ. Microbiol. 2001 3:619-629, Mehlmann et al, Anal. Biochem. 2005 347:316-323, Nguyen Nucleic Acids Res. 2000 28:3904-3909, Proudnikov Nucleic Acids Res. 2006 24:4535-4542, Small et al, Appl. Environ. Microbiol. 2001 67:4708-4716). In one embodiment, the intact RNA may be fragmented using alkali by, e.g., incubation in NaOH (e.g., 50 mM NaOH) at an elevated temperature (e.g., 55° C.) for a period of time (e.g., 10-30 minutes), as described in Liu et al (Applied and Environmental Microbiology, 2007 73: 73-82). In other embodiments, the fragmentation may be metal ion catalyzed in that the intact RNA may be incubated with a metal ion, e.g, an ion of the lanthanide series or a divalent metal ion such as $Mg^{2+}$ or $Zn^{2+}$ (which may be at a concentration of, e.g., 5 mM to 200 mM) at an elevated temperature (e.g, in the range of 50° C. to 95° C.) for a period of time e.g., 1 minute to 1 hr, as described in, e.g, Brown et al (J. Am. Chem. Soc. 2002 124: 7950-7962). For example, RNA may be fragmented by incubation with 10 mM of zinc sulfate ($ZnSO_4$) or zinc chloride ($ZnCl_2$) in 25 mM of Tris-HCl (pH 7.4) at 60° C. for 30 min, as described by Liu, supra. In another case, the RNA may be incubated with 10 mM $ZnCl_2$ in 10 mM Tris-HCl pH 7 for 15 minutes at 70° C. to produce fragments of 60 to 200 bases in length. Incubation of RNA in 40 mM Tris-acetate pH 8.1, 100 mM KOAc and 30 mM MgOA for 20-30 min at 75° C. results in fragments that are generally between 38 and 150 bases in length, as described by Mehlmann et al (Analytical biochemistry 2005 347: 316-323). All of the incubation periods described above may be altered to increase or decrease the lengths of the fragments that are obtained, as desired. The fragmented sample may contain RNA fragments that are, on average, of a length in the range of 30 to 300 nt in length, e.g., 50 to 200 nt in length.

Since fragmentation using the above methods occurs non-specifically at approximately random positions throughout the RNA, the fragmentation on average occurs in longer RNAs on a per molecule basis because the longer RNA molecules contain more potential sites for fragmentation to occur. For example, fragmentation conditions that fragment RNA to fragments of 60 to 200 bases in length should, on average, fragment an RNA molecule of 3 kb in length at approximately 15 to 50 sites without fragmenting a small RNA of approximately 18-31 nucleotides in length. Fragmentation of an RNA sample that contains long RNA molecules and short RNA molecules therefore results in a fragmented sample that contains: a) fragments of long RNA molecules and b) short RNA molecules which are largely intact. The short RNA molecules in the fragmented sample have defined ends in that the nucleotide sequences at the ends of the molecules are known, whereas the fragments of long RNA (because cleavage is not sequence specific) do not have defined ends. The short RNA molecules are generally unfragmented.

The next step of the method includes contacting the fragmented RNA sample with an adaptor comprising a 5'-phosphate group and/or a 3' terminus comprising either a 2'-PO group and 3'-OH group or a 2',3'-cyclic phosphate group in the presence of a eukaryotic tRNA ligase, thereby producing a ligated RNA sample.

As will be described in greater detail below, the method may be implemented in a variety of different ways. In some embodiments, the adaptor used may have a blocked (i.e., unligatable) 5' terminus and a 3' terminus comprising either a 2'-PO group and 3'-OH group or a 2',3'-cyclic phosphate group. In these embodiments, only the 3' of the adaptor may be to the RNA of the fragmented RNA sample. In embodiments in which a fluorescently labeled adaptor is employed, the adaptor may be labeled at any position. In one embodiment, the 5' terminus of the adaptor may be blocked by the fluorescent tag. The ligation of the adaptor to the RNA labels the RNA in some cases. In other embodiments, the adaptor used may have a 5'-phosphate group and a blocked (i.e., unligatable) 3' terminus so that only the 5' terminus of the adaptor ligates to the RNA of the fragmented RNA sample. In other embodiments, the adaptor used may have a 5'-phosphate group and a 3' terminus comprising either a 2'-PO group and 3'-OH group or a 2',3'-cyclic phosphate group so that both ends of the adaptor can ligate to the RNA of the fragmented RNA sample.

Eukaryotic tRNA ligase have evolved to specifically catalyze the repair and joining of tRNA that has been cut, either deliberately (by excision of a tRNA intron as a normal part of tRNA biosynthesis) or defensively (due to the action of some exogenous ribotoxins). In contrast to bacteriophage T4 RNA ligase, the manner in which eukaryotic tRNA ligase recognizes cleaved tRNA substrates has been shown to be independent of the sequence or structure of tRNA. Instead, the ligation substrate specificity of eukaryotic tRNA ligase depends exclusively on the presence of an unusual nucleotide modification (a 2'PO,3'OH group) at the terminus of the upstream tRNA fragment (See FIG. 1). Thus, providing eukaryotic tRNA ligase with a synthesized RNA oligonucleotide containing a 2'-PO,3'-OH group will result in the ligation of this synthetic oligonucleotide to the 5' terminus of any recipient RNA containing a 5'-phosphate group, regardless of its sequence or structure.

The exploitation of RNL enzymatic activities to generate tagged RNA libraries can in certain instances provide advantages over other methods. First, total RNA (both large and small) can be simultaneously labeled in the same reaction using eukaryotic tRNA ligase. Second, only one enzyme addition step is required, which significantly shortens each of the current individual RNA library creation protocols and thus decreases the requisite level of technical proficiency for the user. Third, in contrast to bacteriophage T4 RNA ligase, the unique RNA sequence- and RNA structure-independent substrate recognition mechanism of eukaryotic tRNA ligase is ideally suited for complex RNA library production. Fourth, labeling miRNAs at their 5'-end (in contrast to the current protocols in which miRNAs are labeled at the 3' end) circumvents potential current microarray hybridization problems associated with the heterogeneous sequence content at the 3' ends of some miRNAs (which can create mismatches with microarray probe sequences). Fifth, unlike current mRNA expression microarray profiling protocols, total RNA library production by eukaryotic tRNA ligase does not require library amplification, thus the resultant data will not be distorted by amplification artifacts.

The eukaryotic tRNA ligase used in the method may be tailored to the way in which the method is implemented. For example, if the kinase activity of the enzyme is not desired, it may be inactivated by an alteration in the amino acid sequence of the kinase domain of the enzyme. Likewise, if the cyclic phosphodiesterase activity of the enzyme is not desired, it may be inactivated by an alteration in the amino acid sequence of the cyclic phosphodiesterase domain of the enzyme. As noted above, the eukaryotic tRNA ligase used in the method may minimally have a ligase domain having an amino acid sequence that is at least 80% to the amino acid of the ligase domain of a wild type eukaryotic tRNA ligase. In particular embodiments, the ligase domain of the enzyme used may have an amino acid sequence that is at least 85%, at least 90%, at least 95% or up to 100% identical to the amino acid sequence of the ligase domain of a wild type eukayotic tRNA ligase. If the kinase and cyclic phosphodiesterase domains are present, then they may have at least 85%, at least 90%, at least 95% or up to 100% identical to the amino acid sequence of the domains of a wild type eukayotic tRNA ligase. Since these enzymes are modular, then the enzyme used may have chimeric sequences from different species. For example, in one embodiment, the enzyme used may have: a) a ligase domain that is at least 80% identical to the ligase domain of a eukaryotic tRNA ligase from a first species and, optionally, b) a cyclic phosphodiesterase domain that is at least 80% identical to the cyclic phosphodiesterase domain of a eukaryotic tRNA ligase from a second species and/or c) a kinase domain that is at least 80% identical to the kinase domain of a eukaryotic tRNA ligase from a third species. Guidance for which amino acids to change in order to inactivate the kinase and/or cyclic phosphodiesterase activities of a eukaryotic tRNA ligase can be obtained from published material about those enzymes, as well as what is known about other kinases and cyclic phosphodiesterases. In particular cases, the ligation may be done in the presence or absence of ATP.

Figure 3:
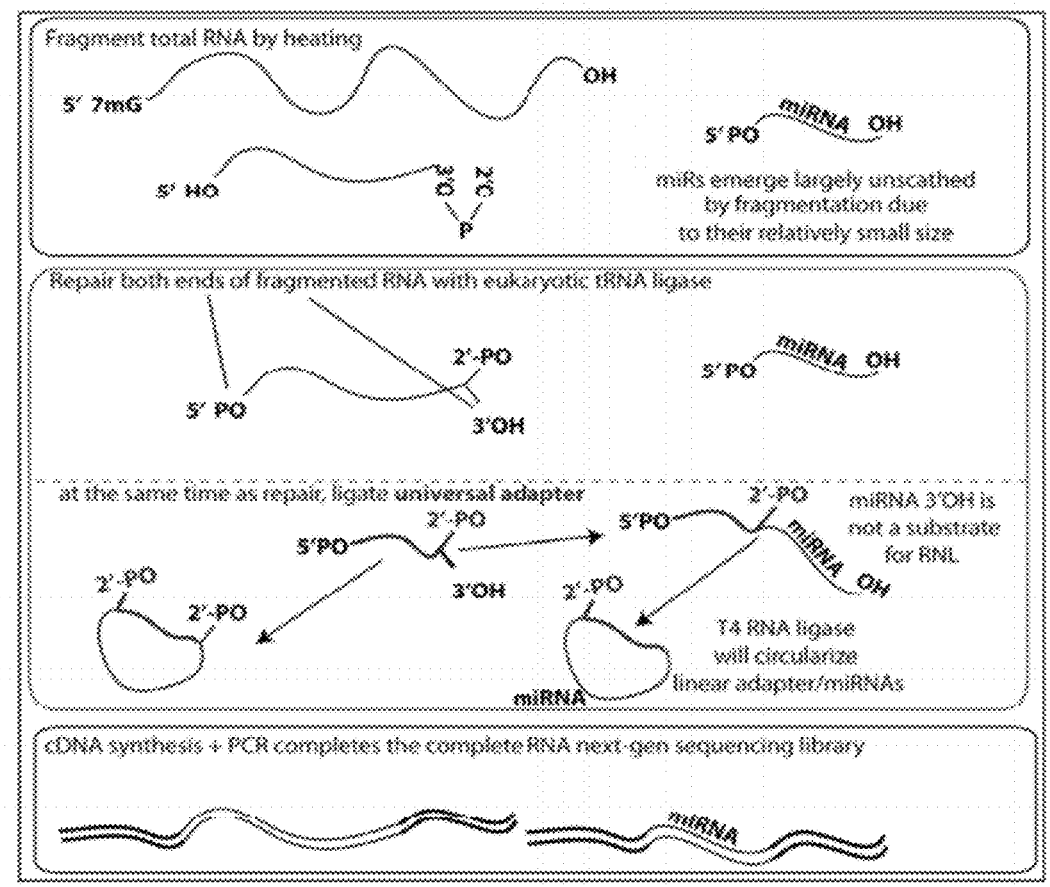
FIG. 3 schematically illustrates a method by which eukaryotic tRNA ligase is used to generate a total RNA library suitable for high throughput sequencing.
Figure 4:
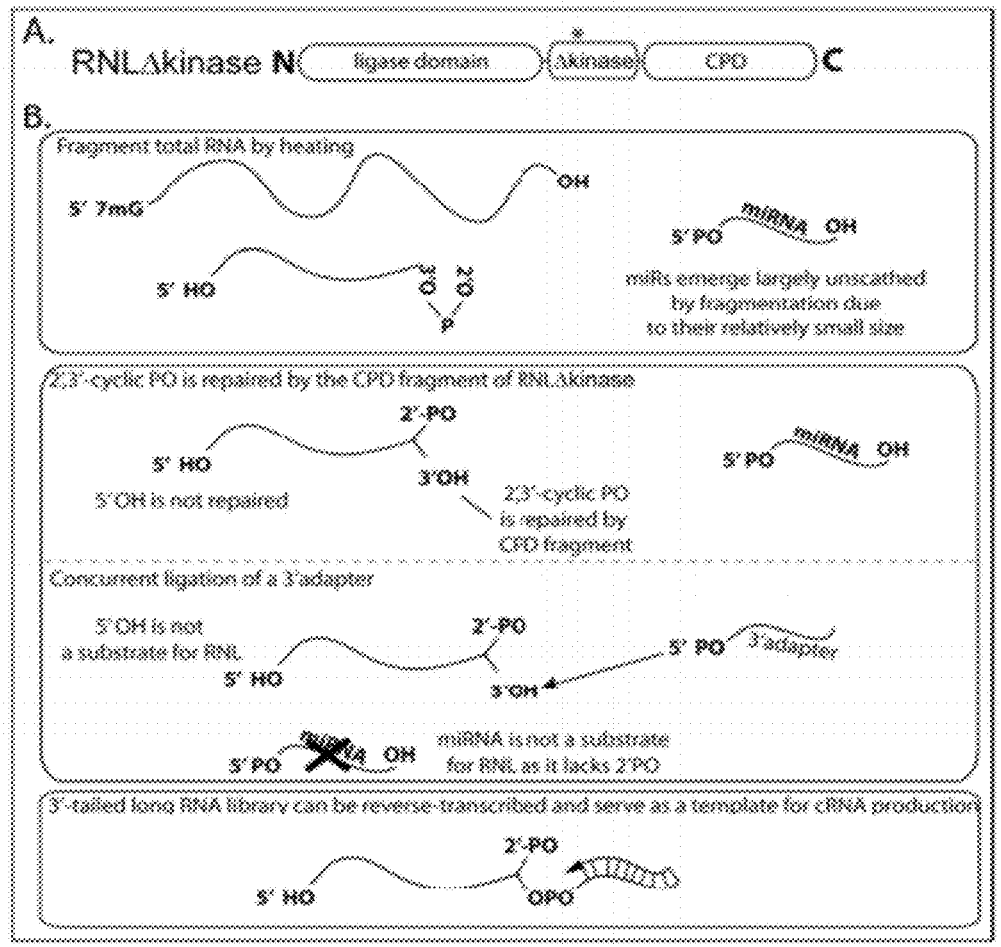
FIGS. 4A and 4B.

As noted above, the method may be implemented in a variety of different ways. In one implementation, the method may be employed in (I) the rapid production of a 5'-labeled total RNA library suitable for hybridization to an array in as few as two steps (illustrated in FIG. 2). An additional implementation (II) of the method is to perform an additional 3'-adapter ligation step by using a mixture of eukaryotic tRNA ligase and T4 RNA ligase; the resultant synthetic oligonucleotide-flanked total RNA library can be copied into cDNA by reverse transcriptase and subject to next-generation sequencing on any of the available platforms (FIG. 3). Alternatively, if the end user was only interested in mRNA profiling by using a array platform optimized for cRNA, this method can be adapted to rapidly produce a 3'-labeled mRNA library (lacking miRNAs), which could then be converted to cRNA and hybridized to a microarray (FIG. 4). These embodiments are described in greater detail below.

In some embodiments (and as illustrated by example in FIG. 2), the method may be employed to add an adaptor to the 5' ends of both short RNAs and fragmented long RNAs. In this embodiment, the eukaryotic tRNA ligase may have kinase activity but no cyclic phosphodiesterase activity and the adaptor may comprise an blocked (i.e., unligateabe) 5' terminus and a 3' terminus comprising a 2'-PO group and a 3'-OH group. In this embodiment, the kinase activity converts the 5'-OH group of the fragments to 5'-PO group and the contacting results in ligation of the 3' terminus of the adaptor to: i. the 5' terminus but not the 3' terminus of the RNA fragments and ii. the 5' terminus but not the 3' terminus of the short RNA molecules. In some embodiments, the adaptor may be labeled at any position and in particular embodiments, the adaptor may be labeled at its 5' end, where the label makes the 5' terminus of the adaptor unligatable.

Figure 2:
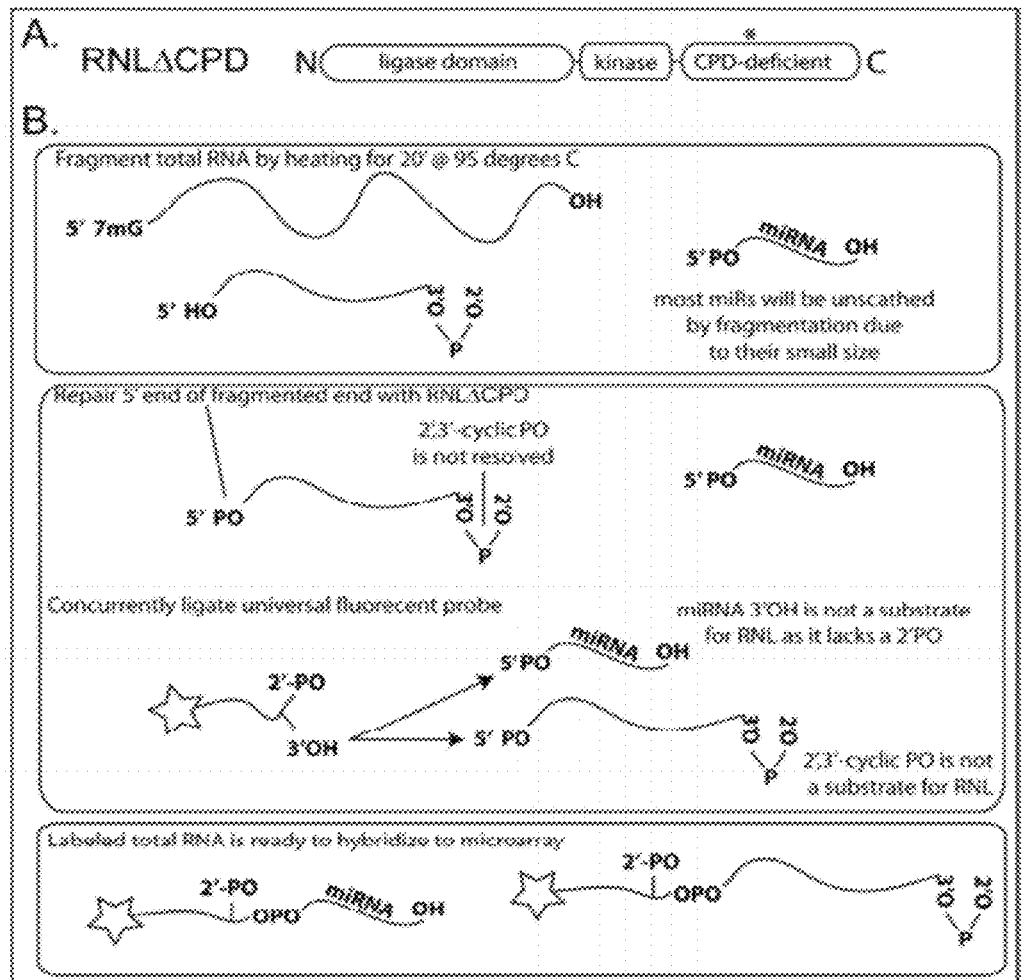
FIGS. 2A and 2B.

FIG. 2 schematically illustrates an exemplary way in which this method may be implemented. With reference to FIG. 2, a total RNA sample is suspended in 1× eukaryotic tRNA ligase buffer that contains 10 mM $MgCl_2$. The resuspended total RNA sample is first fragmented by heating the mixture at 95° C. for 20 minutes. A 5' fluorophore-conjugated oligonucleotide adapter harboring a 2'-PO,3'-OH group (i.e., a resolved 2',3'-cyclic phosphate group) and RNLΔCPD harboring a point mutation that inactivates the cyclic phosphodiesterase domain are added. Since the cyclic phosphodiesterase domain is inactive, the 2',3'-cyclic phosphate group at the 3' terminus of the fragmented large RNA is not repaired by the enzyme. The kinase domain of RNLΔCPD attaches a phosphate group to the 5' terminus of the fragmented large RNA. The miRNAs (which contain a native 5'-PO group) and repaired large RNA are ligated to the 5' fluorophore-conjugated 2'-P,3'-OH group-containing adapter. This adapter will aid in lengthening the miRNAs such that they can be hybridized to an Agilent microarray at a higher Tm to increase specificity, which will be designed with suitable probes to accommodate the ligated adapter. Additionally, there should be little or no unwated ligation (for example, between miRNAs and fragmented larger RNAs), as the 3' terminus of each type of RNA will not be recognized by RNLΔCPD. The reported high specific activity of RNL should enable efficient ligation, thus small amounts of total RNA can be profiled. Also, the 5'-fluorophore-conjugated adapter can be decorated with multiple fluorophores to amplify detectable signal. Finally, since this is a direct RNA profiling approach, amplification artifacts are avoided.

After adaptor ligation, the adaptor-ligated sample is hybridized to an array of nucleic acid probes, and the array is read to obtain an estimate of the abundance of a long RNA in the initial RNA sample and an estimate of the abundance of a short RNA in the initial RNA sample. In particular embodiments, the array is read to independently obtain estimates of the abundance of a plurality of (i.e., at least 10, at least 100, at least 500, at least 1,000, at least 10,000, or at least 50,000 up to at least 100,000) different long RNAs and different short RNAs in the initial RNA sample. The nucleic acid probes that are for detection of the small RNA contain a sequence that is complementary to the short RNA as well as a sequence that is complementary to the adaptor sequence, while the nucleic acid probes that are for detection of the long RNA contain a sequence that is complementary to the long RNA but not a sequence that is complementary to the adaptor.

Specifically, after ligation of the adaptor, the adaptor-ligated sample contains: i. adaptor-ligated short RNA that contain an adaptor portion and a short RNA portion; and ii. adaptor-ligated long RNA fragments comprising an adaptor portion and a long RNA portion. The adaptor-ligated sample is hybridized with array that contains: a i. a first nucleic acid probe that contains a nucleotide sequence that is complementary to both the adaptor portion and of the RNA portion of the adaptor-ligated short RNA; and ii. a second probe that contains a nucleotide sequence that is complementary to the long RNA portion of the adaptor-ligated long RNA but not the adaptor portion of the adaptor-ligated long RNA.

The addition of the adaptor to the short RNA and inclusion of the adaptor sequence in the nucleic acid probe effectively increases length of the complementary region between the short RNA and the complementary probe (which may be as long as 25-40 base pairs as opposed to 18-25 base pairs without the adaptor), thereby increasing the $T_m$ of the hybrid formed between the short RNA and corresponding probe. This allows hybridization to be done at a higher temperature, and also allows a majority of the probes on the array (i.e., probes corresponding to long RNAs as well as probes corresponding to short RNAs) to be temperature matched. Since the long RNAs are fragmented approximately randomly, the addition of the adaptor to the long RNAs is at random positions and, as such, there is no need or advantage for the probes corresponding to the long RNAs to contain a sequence that is complementary to the adaptor.

Suitable labels include fluorescent dyes that include xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4',5'-dichloro-2', 7'-dimethoxyfluorescein (JOE or J), N,N,N', N'-tetramethyl-6-carboxyrhodamine (TAMRA or T), 6-carboxy-X-rhodamine (ROX or R), 5-carboxyrhodamine-6G ($R6G^5$ or $G^5$), 6-carboxyrhodamine-6G ($R6G^6$ or $G^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in some applications include: pyrene, coumarin, diethylaminocoumarin, FAM, fluorescein chlorotriazinyl, R110, eosin, JOE, R6G, tetramethylrhodamine, TAMRA, lissamine, ROX, napthofluorescein, Texas red, napthofluorescein, Cy3, and Cy5, etc.

Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002).

In certain cases, the RNA may by labeled using the Universal Linkage System (ULS™, KREATECH Diagnostics; van Gijlswijk et al Universal Linkage System: versatile nucleic acid labeling technique Expert Rev. Mol. Diagn. 2001 1:81-91). In brief, ULS™ labeling is based on the stable binding properties of platinum (II) to nucleic acids. The ULS molecule consists of a monofunctional platinum complex coupled to a detectable molecule of choice. Alternative methods may be used for labeling the RNA, for example, as set out in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). In embodiments in which a ULS labeling protocol is employed, the labeled RNA may be fragmented as part of the ULS labeling method, which may result in the RNA fragments.

In other embodiments (and as illustrated by example in FIG. 3), the method may be employed to make total RNA libraries for use in next generation sequencing. In this embodiment, the eukaryotic tRNA ligase has kinase activity and cyclic phosphodiesterase activity, and the adaptor contains a 5'-PO group and a 3' terminus comprising either i. a 2'-PO group and 3'-OH group or ii. a 2',3'-cyclic phosphate group. In these embodiments, the kinase activity converts the 5'-OH group of the RNA fragments to 5'-PO and the cyclic phosphodiesterase activity converts the 2'-3'-cyclic phosphate group (of the fragments and, optionally, of the adaptor) to a 2'-PO group and 3'-OH group. In this method, the contacting results the production of: i. circular RNA molecules each comprising an adaptor and an RNA fragment and ii. linear RNA molecules comprising an adaptor and a short RNA. In particular cases, the contacting may done in the presence of a second adaptor, and the resulting circular molecules may comprise the second adaptor in addition to the first adaptor and the short RNA. These embodiments of the method may further comprise contacting the linear RNA molecules with a T4 RNA ligase, thereby resulting in circular molecules comprising adaptor and short RNA. This ligation step may also be done in the presence of a second adaptor.

FIG. 3 schematically illustrates one exemplary way in which this method may be implemented. With reference to FIG. 3, a total RNA sample is prepared as described in the method described above, except the adapter does not contain a blocked 5' end. Intermolecular ligation of the adapter sequence will create circular adapter/RNAs, which can be primed for cDNA synthesis, digested with a restriction endonuclease and PCR amplified to create a library that will be input into the next-generation sequencer. As the miRNAs lack a 2'PO,3'OH group (and are therefore not substrates for the ligase activity), T4 RNA ligase may be added after RNL to close the circular adapter/miRNAs.

By providing a molar excess of adapter in the total RNA mix, the common products of ligation with the adapter should be (i) adapter/RNA circles, (ii) adapter-multimer/RNA circles and (iii) adapter multimer circles devoid of RNA. During reverse-transcription, the 'empty' adapter multimers will be cut after cDNA synthesis by engineering a unique restriction site that is created when adapters are ligated head-to-tail, thus PCR amplification of the adapter-adapter cDNA will be significantly reduced. As an additional consequence of this digestion, the adapter-multimer/RNA circles can be resolved into linear single adapter/RNAs, which are the same as in the method described above.

In particular cases and depending on the conditions used, the product of this ligation may include a multimer of the structure [adaptor-fragment-]$_n$ that result from the head-to-tail ligation of free ends. As the adaptors may be in molar excess, linker-linker-linker multimers may also be presennt and that the individual sequenceable units may be the result of reverse transcriptase bumping into an upstream, oligonucleotide that is annealed to the ligated adaptor. These long multimers could either be circular (if no short RNAs are included), or the linear short RNAs could 'cap' the 3' end (because the 3'-OH would be unligatable by tRNA ligase).

The product generated by this method is general compatible with one or more next-generation sequencing platforms. In certain embodiments, the products may be clonally amplified in vitro, e.g., using emulsion PCR or by bridge PCR, and then sequenced using, e.g., a reversible terminator method (Illumina and Helicos), by pyrosequencing (454) or by sequencing by ligation (SOLiD). Examples of such methods are described in the following references: Margulies et al (Genome sequencing in microfabricated high-density picoliter reactors". Nature 2005 437: 376-80); Ronaghi et al (Real-time DNA sequencing using detection of pyrophosphate release Analytical Biochemistry 1996 242: 84-9); Shendure (Accurate Multiplex Polony Sequencing of an Evolved Bacterial Genome Science 2005 309: 1728); Imelfort et al (De novo sequencing of plant genomes using second-generation technologies Brief Bioinform. 2009 10:609-18); Fox et al (Applications of ultra-high-throughput sequencing. Methods Mol Biol. 2009; 553:79-108); Appleby et al (New technologies for ultra-high throughput genotyping in plants. Methods Mol Biol. 2009; 513:19-39) and Morozova (Applications of next-generation sequencing technologies in functional genomics. Genomics. 2008 92:255-64), which are incorporated by reference for the general descriptions of the methods and the particular steps of the methods, including all starting products, reagents, and final products for each of the steps. The methods described above may be employed to investigate any genome, of known or unknown sequence, e.g., the genome of a plant (monocot or dicot), an animal such a vertebrate, e.g., a mammal (human, mouse, rat, etc), amphibian, reptile, fish, birds or invertebrate (such as an insect), or a microorganism such as a bacterium or yeast, etc.

In other embodiments (and as illustrated by example in FIG. 4), the method may be employed to make tailed RNA libraries suitable for cRNA production. In this embodiment, the eukaryotic tRNA ligase may have cyclic phosphodiesterase activity but no kinase activity; and the adaptor may comprise a 5' phosphate and an unligatable 3' end. In this embodiment, cyclic phosphodiesterase activity converts the 2'-3'-cyclic phosphate group (of the fragments and, optionally of the adaptor) to a 2'-PO group and 3'-OH group. The contacting results in ligation of the 5' terminus of the adaptor to: i. the 3' terminus but not the 5' terminus of the RNA fragments and ii. neither the 3' terminus nor the 5' terminus of the short RNA molecules. In particular cases, the adaptor may comprise a sequence for a bacteriophage RNA polymerase promoter, thereby allowing the ligated fragments to be amplified using a bacteriophage RNA polymerase (e.g., from T3 or T7, etc.).

FIG. 4 schematically illustrates one exemplary way in which this method may be implemented. With reference to FIG. 4, a modified eukaryotic tRNA ligase is used to rapidly prepare 3'-tailed mRNA/ncRNA libraries suitable for cRNA production. If the end user is uninterested in miRNA profiling and wishes to rapidly obtain an amplified cRNA library, RNLAkinase can be used according to the outline in FIG. 4. RNA is fragmented and the RNLAkinase is added concurrently with a 3' adapter oligonucleotide containing a T7 RNA polymerase promoter element. RNLAkinase will resolve the 2',3'-cyclic phosphate group but not the 5'OH group and the ligase domain will attach the 3' adapter to the 2'-PO-containing fragmented RNA terminus. The miRNA will not be ligated as it lacks a 2'-PO group at its terminus. To make cDNA, the 3'-adapter ligated long RNAs can be reverse transcribed by addition of a primer that hybridizes to the 3' adapter and reverse-transcriptase. The resultant cDNA can serve as a template for RNA production by the addition of T7 RNA polymerase.

Additional Embodiments

In an additional embodiment, the eukaryotic tRNA ligase may be employed to ligate one or more appropriately designed adaptors to an unfragmented RNA sample, e.g., total RNA that has not undergone any fragmentation procedure. In these embodiments, the sample may comprise: i. unfragmented long RNA molecules (which may contain, e.g., a 5' m$^7$G cap and ii. unfragmented short RNA molecules that comprise a 5' phosphate group and a 3' OH group. In these embodiments, the adaptor may comprise a 2'-PO group and 3'-OH group or a 2',3'-cyclic phosphate group. The 5' end of this adaptor may be blocked, e.g., with a label or an affinity tag, thereby allowing the adaptor to ligate to only the short RNA molecules. This method may include: a) obtaining an unfragmented RNA sample comprising: i. long RNA molecules; and ii. short RNA molecules that comprise a 5' phosphate group and a 3' OH group; and b) contacting the unfragmented RNA sample with an adaptor comprising a blocked 5' end and either a 2'-PO group and 3'-OH group or a 2',3'-cyclic phosphate group in the presence of a eukaryotic tRNA ligase, thereby producing a ligated RNA sample in which the short RNA molecules are selectively ligated to the adaptor.

In any embodiment including the embodiment described above, a ligation product may be directly hybridized to an array (e.g., if the first adaptor is labeled) or purified away from other products in the same (e.g., if the first adaptor has an affinity tag, e.g., a "biotin moiety" i.e., an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12). Alternatively, a ligated adaptor may contain a RNA polymerase promoter that after first- and second-strand cDNA synthesis, may be sequenced or used to direct transcription of the adaptor-ligated RNAs; these transcribed RNAs can be labeled with a fluorescent dye during transcription and the sample can be hybridized to an array to detect the amplified, labeled RNA molecules.

In some embodiments, fragmented longer RNAs and unfragmented short RNAs in a sample may be sequenced, e.g., using a next-generation sequencing technology. To perform such a method, RNA may be reverse transcribed into cDNA that contains adaptors that flank the RNAs to be sequenced. The flanking adaptors are used to prime the sequencing reaction.

Figure 11:
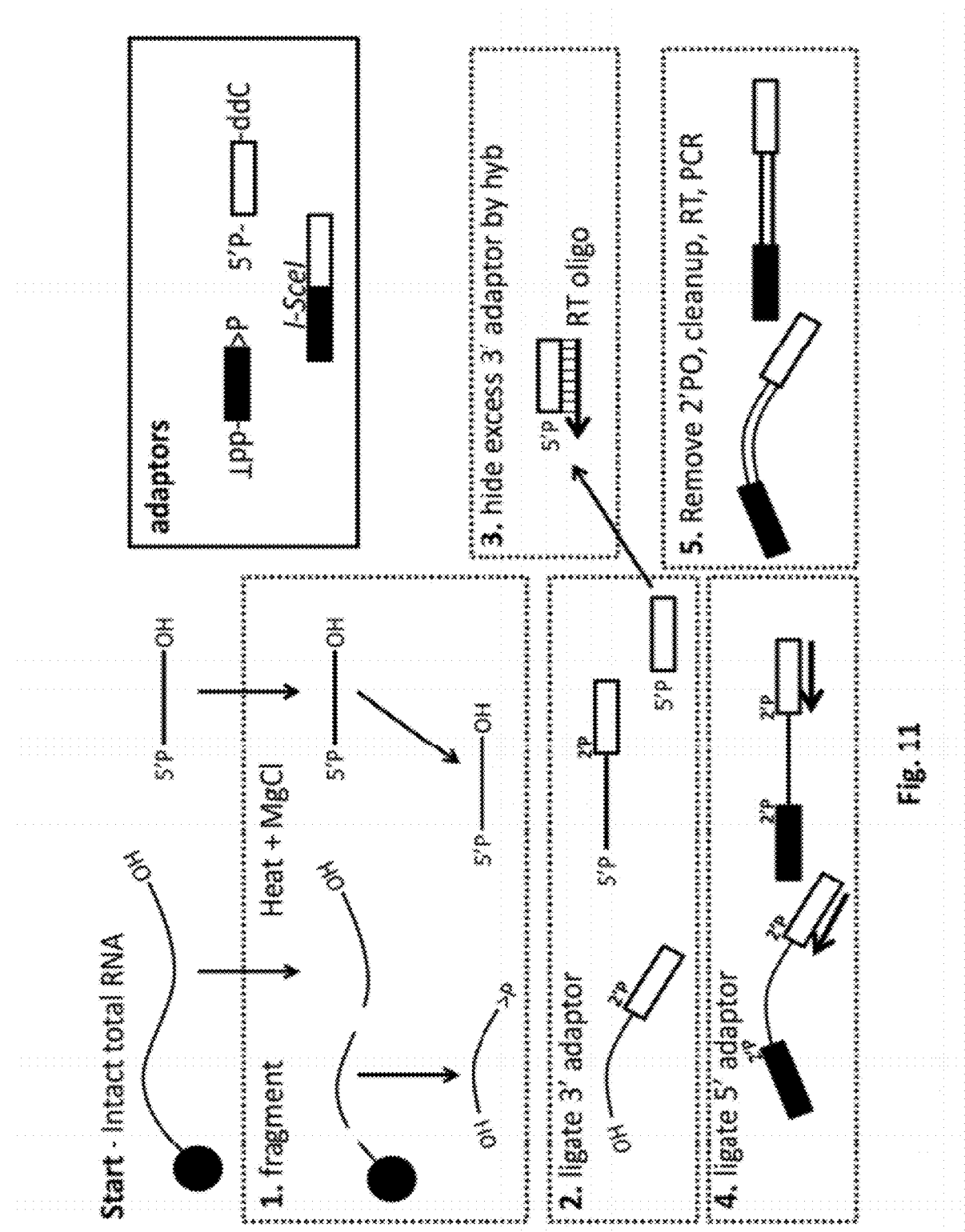
FIG. 11 schematically shows an exemplary method for producing adaptor ligated RNA.

There are several ways to join adaptors to each end of the RNA to be sequenced. One method involves random priming using a first adaptor to make cDNA, and then ligating the cDNA and the other adaptor. In another method, the adaptors are directly added to the RNA prior to cDNA synthesis. This technique is called "direct adaptor ligation". An example of such a method is schematically illustrated in FIG. 11.

The direct adaptor ligation method is favored because it allows: a) the production of directional RNA libraries that map sequence to a strand (which information is technically challenging to preserve if random priming is used to generate cDNA) and b) the profiling of small RNAs such as microRNAs and other classes of small RNA (which are too small to random prime). However, adaptor ligation methods often produce an unwanted by product produced by ligation of the 5' adaptor (i.e., the adaptor that ligates to the 5' end of the RNA) to the 3' adaptor (i.e., the adaptor that ligates to the 3' end of the RNA). These products are often referred to as "adaptor-dimers" and are a constant source of inefficiency because they contain no information about the transcriptome being sequenced.

The following methods are ways in which adaptor dimers can be removed from or avoided during cDNA library production.

Figure 9:
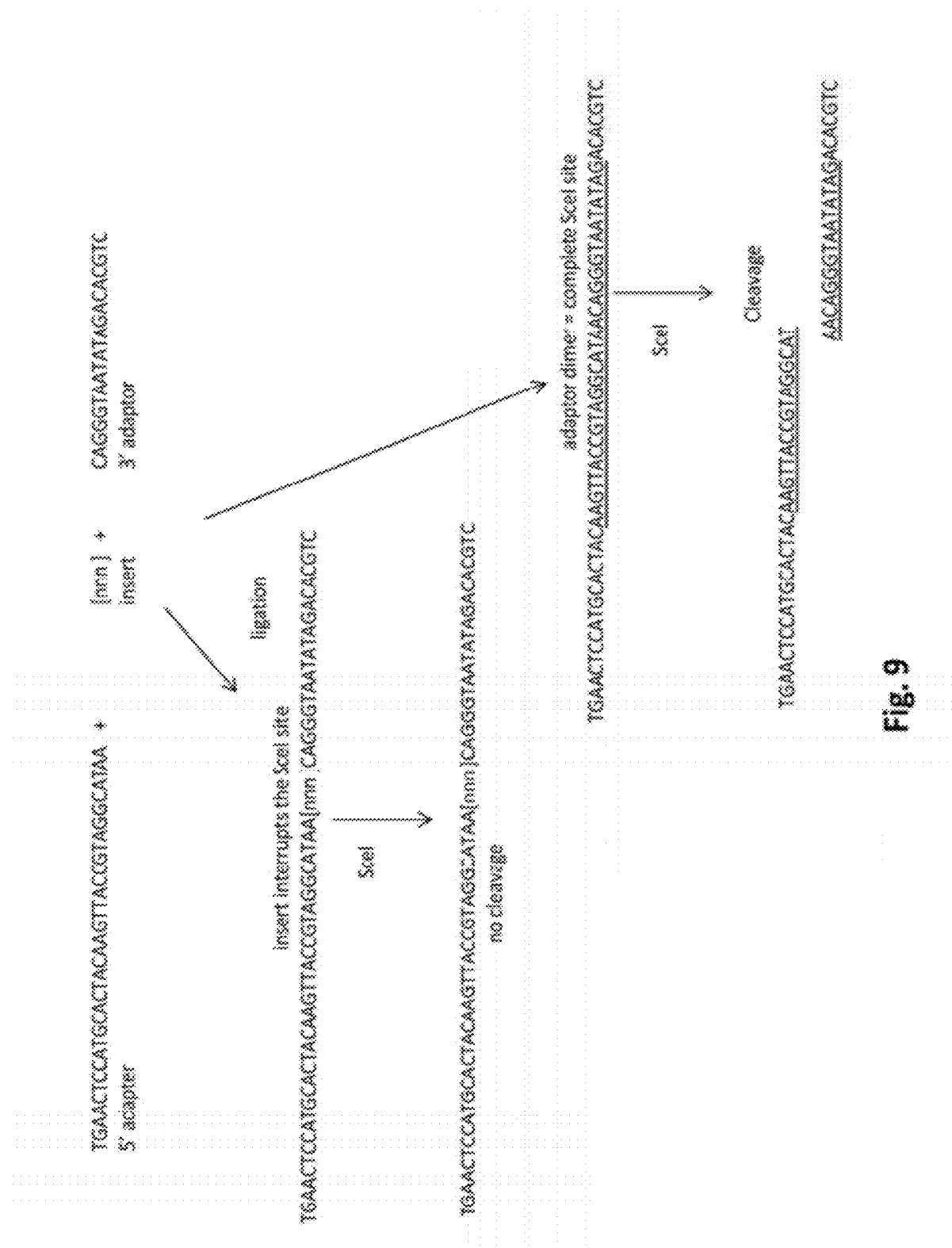
FIG. 9 schematically illustrates an embodiment that involves a homing endonuclease. From top to bottom: SEQ ID NOS: 1-7.

In one embodiment and as illustrated in FIG. 9, the 5' adaptor and the 3' adaptor can be designed that they each contain a partial recognition sequence for a homing endonuclease and that when they are ligated together to produce an adaptor dimer and present in double stranded form, the adaptor dimer contains a homing endonuclease recognition site. Homing endonucleases differ from restriction endonucleases in that they recognize DNA sequence elements in the 20 to 30 nucleotide size rage, and their recognition sequences are non-palindromic. As such, in many mammalian genomes, there may be zero or one target site for a homing endonuclease. Exemplary homing endonucleases include those in the following families: LAGLIDADG, GIY-YIG, His-Cys box, H-N-H, PD-(D/E)xK and Vsr-like. SceI is an example of an enzyme that could be used, although many others exist.

In this embodiment and as illustrated in FIG. 9, adaptors can be added to a ligation reaction that can produce two possible ligation products. As shown on the left of FIG. 9, an RNA insert is been ligated to a 5' adaptor and a 3' adaptor. Alternatively (as shown on the right of FIG. 9) no insert has been ligated, and the adaptors directly ligate to one another to produce an adaptor dimer. After first and second strand cDNA synthesis, the ligated products will be double-stranded cDNA. Addition of the homing endonuclease SceI results in cleavage of the adaptor-dimers (right), and the insert-containing products (left) are not cleaved. The cleaved adaptor dimers can be purified away from the indigested products by size or by charge. Alternatively or in addition, after digestion, the double stranded products may be amplified by PCR which should yield an excess of inserts that are flanked by adaptors, but virtually no adaptor-dimers. The amplified cDNAs can then be sequenced on any suitable sequencing platform.

The method may comprise: a) obtaining a first single stranded adaptor and a second single stranded adaptor, wherein the first adaptor and the second adaptors each contain partial recognition sites for a homing endonuclease and, when ligated together, provide an adaptor dimer containing a recognition site for said homing endonuclease; b) ligating said first single stranded adaptor to a first end the of the RNA molecules of an RNA sample; c) ligating said second adaptor to the end the of the RNA molecules in said sample; d) producing double stranded cDNA from the product of step c); and e) cleaving said double stranded cDNA using said homing endonuclease, thereby removing adaptor dimers from the sample. This method may further include subjecting the cleaved sample to PCR using primers that anneal to the adaptor sequences.

In an alternative embodiment, the substrate preference of eukaryotic tRNA ligase for single-stranded ends may be exploited. In these embodiments the method involves: ligating one adaptor (e.g., the 3' adaptor) the RNA and, after ligation, hybridizing a complementary oligonucleotide to the remaining unligated adaptor in order to "hide" it from the ligase. Next, the other adaptor (e.g., the 5' adaptor) is ligated using a eukaryotic tRNA ligase. Because the first adaptor has a double stranded end, it is effectively hidden from the ligase, and not used in the production of adaptor dimers. In these embodiments, the complementary oligonucleotide may be added at a molar excess to the adaptor that it is designed to block, e.g., by at least 2-fold, by at least 5-fold, by at least 10-fold, by at least 50-fold, by at least 100-fold or by at least 1,000-fold or more. When duplexed with the complementary oligonucleotide, the 5' end of the adaptor may be flush or recessed relative to the end of the complementary oligonucleotide, thereby rendering it inaccessible to the ligase. As would be readily apparent, the complementary oligonucleotide may be appropriately blocked at its termini so that it, itself, does not interfere with the ligation. The method may comprise: a) ligating the first single stranded adaptor to a first end the of the RNA molecules of an RNA sample; b) hybridizing the first single stranded adaptor to a complementary oligonucleotide to make a duplex that does not contain an ligatable overhang of the single stranded adaptor thereby removing the first single stranded adaptor as a substrate for a future ligation; and c) ligating a second adaptor to the other end the of the RNA molecules in the RNA sample using a eukaryotic tRNA ligase, thereby producing an RNA sample that has adaptors ligated to both ends, is therefore provided.

Kits

Also provided by the subject invention are kits for practicing the subject methods, as described above. In certain embodiments, the subject kits contain at least: a) an adaptor comprising a 5'-PO group and/or a 3' terminus comprising i. a 2'-PO group and 3'-OH group or ii. a 2',3'-cyclic phosphate group; and b) a eukaryotic tRNA ligase. The kit may also contain reagents for isolating RNAs from a cell, reagents for labeling a RNA, reagents for hybridizing labeled small RNAs to an array, a control RNA, and reagents for fragmenting RNA etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods may be employed in a variety of diagnostic, drug discovery, and research applications that include, but are not limited to: high throughput sequencing, genotyping, and gene expression analysis. In particular embodiments, the method may be employed in the diagnosis or monitoring of a disease or condition (where the expression of short and/or long RNAs provide a marker for the disease or condition), discovery of drug targets (where a short and/or long RNA is differentially expressed in a disease or condition and may be targeted for drug therapy), drug screening (where the effects of a drug are monitored by assessing the level of a short and/or long RNA), determining drug susceptibility (where drug susceptibility is associated with a particular profile of a short and/or long RNA) and basic research (where is it desirable to identify the presence of short and/or long RNAs in a sample, or, in certain embodiments, the relative levels of a particular short and/or long RNAs in two or more samples).

In certain embodiments, relative levels of small short and/or long RNAs in two or more different small RNA samples may be obtained using the above methods, and compared. In these embodiments, the results obtained from the above-described methods are usually normalized to the total amount of RNA in the sample or to control RNAs (e.g., constitutive RNAs), and compared. This may be done by comparing ratios, or by any other means. In particular embodiments, the short and/or long RNA profiles of two or more different samples may be compared to identify short and/or long RNAs that are associated with a particular disease or condition (e.g., a short and/or long RNA that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used. Accordingly, among other things, the instant methods may be used to link the expression of certain genes to certain physiological events.

EXAMPLE 1

Materials and Methods

Time-Course of Ligation for Analysis on Denaturing Acrylamide Gel

To determine the in vitro reaction kinetics of AtRNLT1001A, a time-course of ligation was performed. The ligation reactions contained a 5'-blocked (5'-Cy3) substrate RNA oligonucleotide containing a 2'PO, 3'OH downstream terminus and a second RNA oligonucleotide, 5' OH-let-7a-Cy5. These RNA substrates were denatured at 95° C. for 1 min in presence of 50 mM Tris-HCl (pH8) and 10 mM $MgCl_2$, followed by chilling on ice. These oligonucleotides were then incubated with AtRNL T1001A in a 20 ul reaction containing 5 μmoles OH-let-7a-Cy5, 50 mM Tris-HCl pH8, 10 mM $MgCl_2$, 1 mM ATP, 1 mM GTP, 1 nmol Cy3-labeled RNA oligonucleotide, 2.5 μmol AtRNL T1001A, 40U RNase inhibitor, and 2 mM dithiothreitol. Ligation reactions were stopped at different times by the addition of 100% formamide, denatured for 1 min at 95° C., and then chilled on ice. The reactions were subsequently resolved on a 15% denaturing polyacrylamide gel and Cy5 was detected at 650 nm with a PhosphorImager (ABI).

For these reactions, AtRNL T1001A was 2.4 uM. The OH-let-7a-Cy5 is a 22mer RNA oligonucleotide with the sequence 5'-UGA GGU AGU AGG UUG UAU AGU U/3Cy5Sp-3' (SEQ ID NO:8), and the Cy3-labeled RNA oligonucleotide has a sequence of Cy3-UAU UGA CA-3'OH, 2'P.

Total RNA Labeling for Microarray Applications

A sample of purified human total RNA was end-labeled with a 5'-Cy3-labeled RNA-2'PO,3'OH oligonucleotide as follows. 200 ng of purified total RNA was resuspended in 8 ul buffer containing 50 mM Tris-HCl (pH 8), 10 mM $MgCl_2$. The RNA was fragmented by heating the reaction mixture at 95° C. for 10 min and then chilled on ice. The fragmented RNA was then incubated for 30 minutes at 37° C. with AtRNL T1001A and the 5'-Cy3-labeled 8mer RNA oligonucleotide in a 30 ul reaction containing 200 ng of the fragmented RNA, 50 mM Tris-HCl pH8, 10 mM MgCl2, 1 mM ATP, 1 mM GTP, 1 nmol Cy3-RNA oligonucleotide, 2.5 μmol AtRNL T1001A, and 2 mM dithiothreitol. For hybridization, the reaction was resuspended in standard Agilent hybridization buffer to a final volume of 110 ul, denatured 3 minutes at 90° C., and chilled on ice. The sample was then loaded on a DNA microarray containing probes for 17,306 mRNAs (137,526 exons), 5274 long-noncoding RNAs (lincRNAs) (22,134 exons), and 191 miRNAs. The array was then incubated at 65° C. for about 17 hours, and washed according to Agilent's standard gene expression array protocol. The AtRNL T1001A used here is 2.4 uM. The Cy3-labeled RNA oligonucleotide is an 8mer with a 5'-Cy3 and a 3'OH, 2'P (Cy3-UAUUGACA-3'OH, 2'P).

Results

*Arabidopsis* tRNA ligase (AtRNL) was testsed to determine if it could ligate a 5'-Cy3-labeled RNA oligonucleotide with 2' phosphate and 3' hydroxyl groups to a human let-7a RNA substrate with a 5' hydroxyl and a 3' Cy5 fluorescent label. The two RNAs were incubated with AtRNL for 5-60 minutes and the reactions were assayed by gel electrophoresis followed by PhosphorImager analysis (FIG. 5). The reaction was found to proceed very quickly, with 95% of the let-7a RNA substrate phosphorylated and ligated within 15 minutes.

Figure 6:
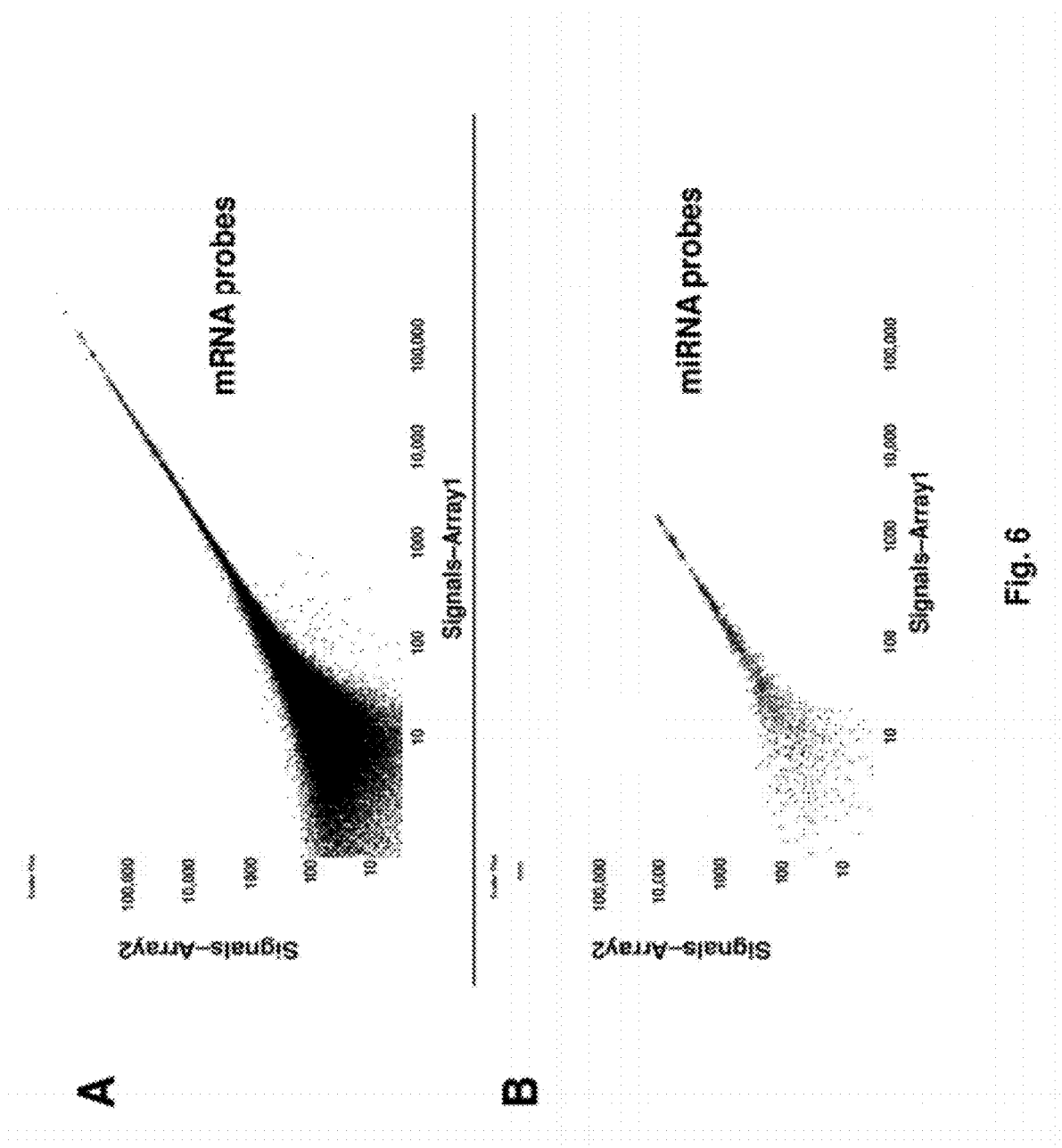
FIG. 6 panels A and B show graphs showing that duplicate assays are highly reproducible.
Figure 7:
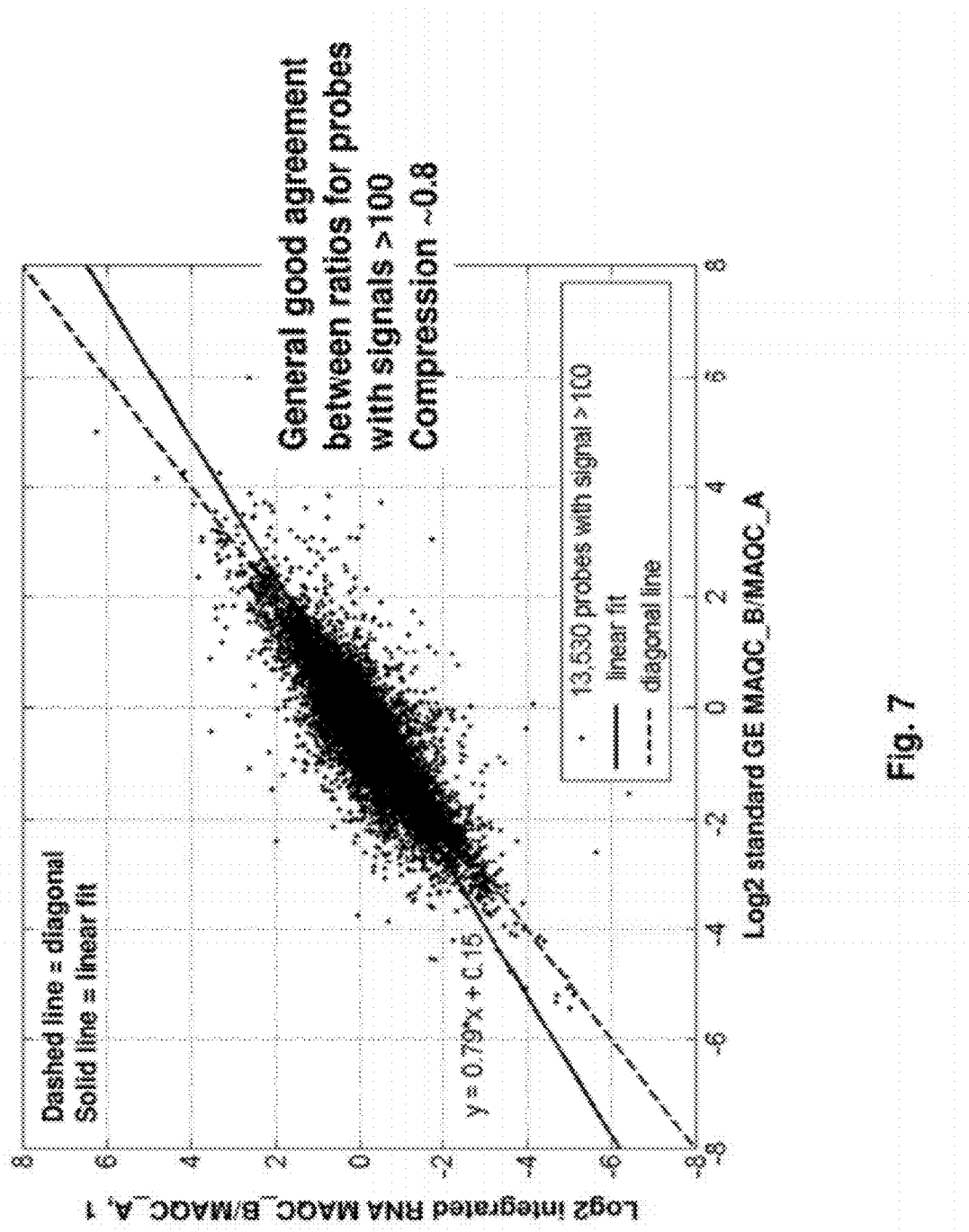
FIG. 7 is a graph showing a comparison of log 2 Ratios of Integrated RNA Assay (1 µg) to standard exon array data, for a total of 72,272 probes.
Figure 8:
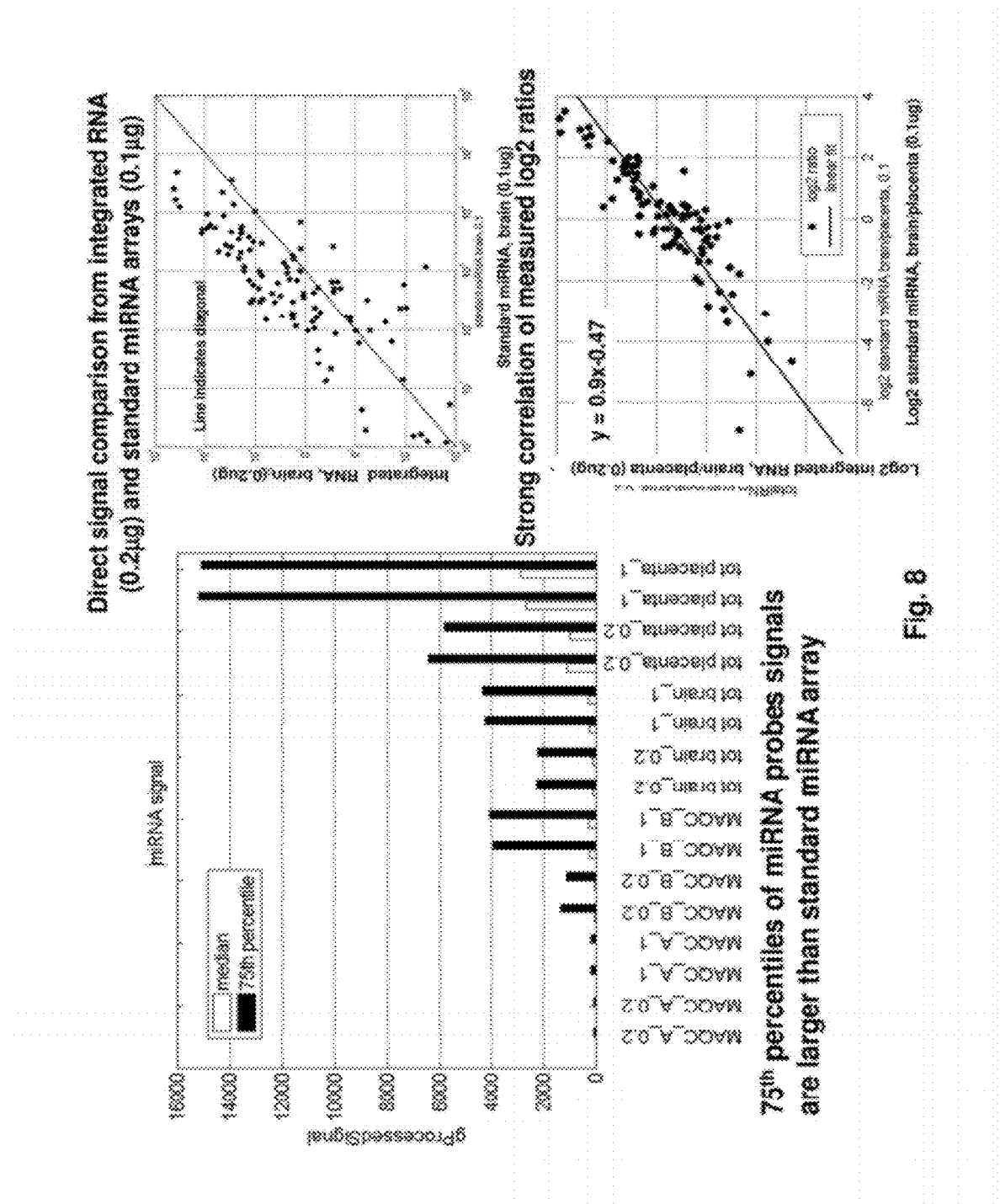
FIG. 8 shows several graphs that provide a comparison of integrated RNA array miRNA data to standard miRNA array.

The assay was run on a total RNA sample. Human total RNA was first fragmented by heating in the presence of magnesium for ten minutes, followed by ligation of the fragments to a 5'-Cy3-labeled RNA oligonucleotide that contained a 2'P, 3'OH using AtRNLT1001A. After ligation, the sample was hybridized to a DNA microarray containing probes for mRNAs, lincRNAs, and microRNAs (miRNAs). After washing and scanning, data from duplicate hybridizations was analyzed (FIG. 6). The plots show signals from the replicate hybridizations plotted against one another for the mRNA probes (FIG. 7) and the miRNA probes (FIG. 8). The linearity of the data indicates the labeling and hybridizations are very reproducible.

EXAMPLE 2

Figure 10:
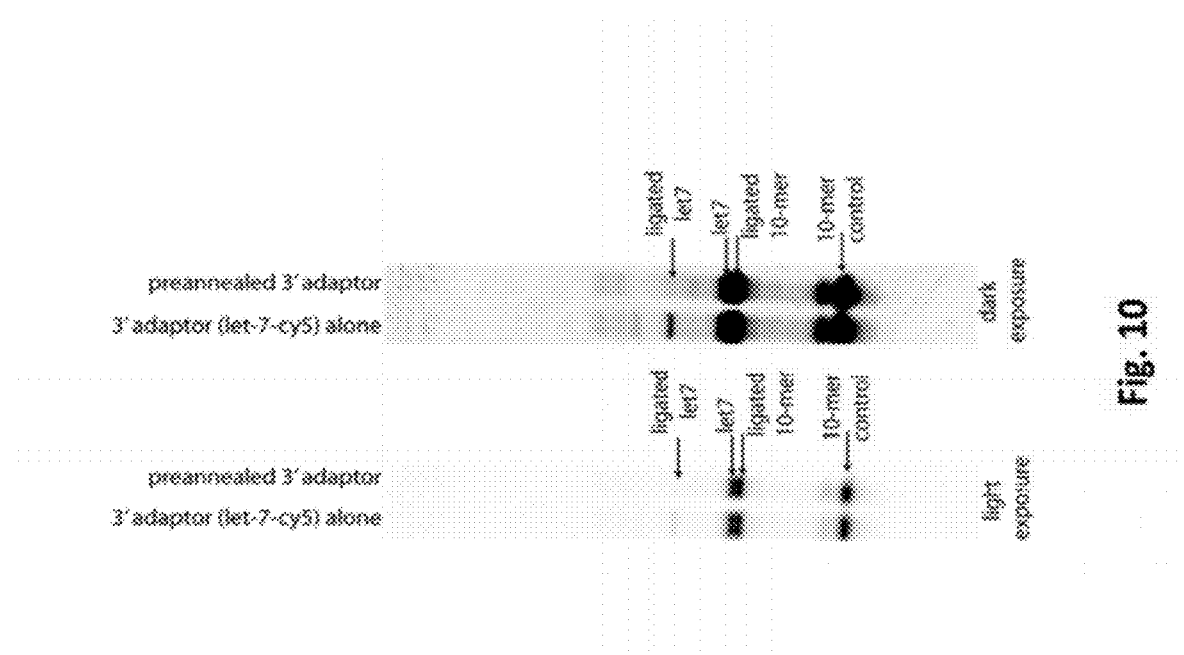
FIG. 10 shows results of a ligation assay.

In the experiment described below, there is one unlabeled 'substrate' RNA (that acts as a proxy for fragmented total RNA) and two 3'-terminal Cy5-labeled oligonucleotides of different lengths and sequences (called let-7a-Cy5 and 10-mer-Cy5). Results are shown in FIG. 10. The left lane contains all three oligos in a standard ligation reaction catalyzed by AtRNL. There are two ligation products visible (as indicated by the ligated let-7 arrow and ligated 10-mer arrow) in this lane. The right lane contains the same three oligos, but with a 10-fold excess of antisense Let-7a that was pre-annealed prior to AtRNL addition.

The results indicate that the 10-mer is ligated to the substrate RNA equally in both reactions. In contrast, a ligation product of substrate+let-7a-Cy5 is only visible in the absence of antisense let-7, showing that AtRNL does not efficiently use double-stranded 3' adaptors in ligation reactions. As the 10-mer is still ligated in these reactions (and is not complementary to the antisense let-7 oligo), the discrimination against the let-7 substrate is likely due to AtRNL having a preference for RNAs that have a single-stranded 5'-phosphate donor end.

The invention claimed is:

1. A method of preparing an RNA sample comprising:
 a) obtaining a fragmented RNA sample comprising:
  i. RNA fragments of long RNA molecules, wherein said fragments comprise a 5'-OH group and a 2'-3'-cyclic phosphate group; and
  ii. unfragmented short RNA molecules that comprise a 5' phosphate group and a 3' OH group; and
 b) contacting said fragmented RNA sample with one or more adaptors comprising an unligatable 5' terminus and a 3' terminus comprising a 2'-PO group and a 3'-OH group in the presence of a eukaryotic tRNA ligase that has a kinase activity but no cyclic phosphodiesterase activity, thereby producing an adaptor ligated RNA sample wherein said kinase activity converts the 5'-OH group of said fragments to 5'-PO group and said contacting results in ligation of the 3' terminus of the adaptor to:
   i. the 5' terminus but not the 3' terminus of the RNA fragments and
   ii. the 5' terminus but not the 3' terminus of the short RNA molecules.

2. The method of claim 1, wherein said fragmented RNA sample is made by exposing an initial RNA sample comprising intact long RNA molecules and unfragmented short RNA molecules to fragmentation conditions that favor fragmentation of said long RNA molecules relative to said short RNAs molecules.

3. The method of claim 2, wherein said exposing comprises contacting said initial RNA sample with a divalent cation at a temperature of at least 50° C.

4. The method of claim 1, wherein said adaptor is labeled.

5. The method of claim 4, wherein said adaptor is labeled at its 5' end.

6. The method of claim 1, wherein said method further comprises, after step b), ligating an adaptor to the 3' end of the RNA molecules.

7. The method of claim 1, wherein said short RNA molecules comprise small RNA molecules selected from the group consisting of short interfering RNA (siRNA) molecules, microRNA (miRNA) molecules, tiny non-coding RNA (tncRNA) molecules, small modulatory RNA (smRNA) molecules and piwi-interacting small RNAs (piRNAs).

8. The method of claim 1, wherein said adaptor is in the range of 6 to 12 nucleotides in length.

9. The method of claim 2, wherein said initial RNA sample comprises total cellular RNA.

10. The method of claim 2, wherein said initial RNA sample comprises total cellular RNA from which tRNA and rRNA has been removed.

11. A method of preparing an RNA sample comprising:
a) obtaining a fragmented RNA sample comprising:
   i. RNA fragments of long RNA molecules, wherein said fragments comprise a 5'-OH group and a 2'-3'-cyclic phosphate group; and
   ii. unfragmented short RNA molecules that comprise a 5' phosphate group and a 3' OH group; and
b) contacting said fragmented RNA sample with one or more adaptors comprising a 5' phosphate group and an unligatable 3' end in the presence of a eukaryotic tRNA ligase that has cyclic phosphodiesterase activity but no kinase activity, thereby producing an adaptor ligated RNA sample wherein said cyclic phosphodiesterase activity converts said 2'-3'-cyclic phosphate group of said adaptor to a 2'-PO group and 3'-OH group and said contacting results in ligation of the 5' terminus of the adaptor to:
   i. the 3' terminus but not the 5' terminus of the RNA fragments and
   ii. neither the 3' terminus nor the 5' terminus of the short RNA molecules.

12. The method of claim 11, wherein said adaptor comprises sequence for a bacteriophage RNA polymerase promoter.

13. The method of claim 11, further comprising amplifying the product of step b using a bacteriophage RNA polymerase.

14. The method of claim 11, wherein said fragmented RNA sample is made by exposing an initial RNA sample comprising intact long RNA molecules and unfragmented short RNA molecules to fragmentation conditions that favor fragmentation of said long RNA molecules relative to said short RNAs molecules.

15. The method of claim 14, wherein said exposing comprises contacting said initial RNA sample with a divalent cation at a temperature of at least 50° C.

16. The method of claim 14, wherein said initial RNA sample comprises total cellular RNA.

17. The method of claim 11, wherein said short RNA molecules comprise small RNA molecules selected from the group consisting of short interfering RNA (siRNA) molecules, microRNA (miRNA) molecules, tiny non-coding RNA (tncRNA) molecules, small modulatory RNA (smRNA) molecules and piwi-interacting small RNAs (piRNAs).

18. The method of claim 11, wherein said adaptor is in the range of 6 to 12 nucleotides in length.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
cagggtaata tagacacgtc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
cagggtaata tagacacgtc                                              20

<210> SEQ ID NO 3
<211> LENGTH: 55
```

```
<212> TYPE: DNA
<213> ORGANISM: Artificial Sequence
<220> FEATURE:
<223> OTHER INFORMATION: Synthetic oligonucleotide

<400> SEQUENCE: 3
tgaactccat gcactacaag ttaccgtagg cataacaggg taatatagac acgtc      55

<210> SEQ ID NO 4
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 4
tgaactccat gcactacaag ttaccgtagg cataacaggg taatatagac acgtc      55

<210> SEQ ID NO 5
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 5
tgaactccat gcactacaag ttaccgtagg cataacaggg taatatagac acgtc      55

<210> SEQ ID NO 6
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 6
tgaactccat gcactacaag ttaccgtagg cat                              33

<210> SEQ ID NO 7
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 7
aacagggtaa tatagacacg tc                                          22

<210> SEQ ID NO 8
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 8
ugagguagua gguuguauag uu                                          22
```